(12) United States Patent
Prinzhorn et al.

(10) Patent No.: US 9,791,419 B2
(45) Date of Patent: Oct. 17, 2017

(54) PHOTO-ACOUSTIC DEVICE AND METHOD FOR NON-CONTACT MEASUREMENT OF THIN LAYERS

(71) Applicant: NOVELIS INC., Atlanta, GA (US)

(72) Inventors: Heinrich Prinzhorn, Gottingen (DE); Stefan Erdmann, Atlanta, GA (US); Thomas Wuttke, Renshausen (DE); Andreas Bauer, Gottingen (DE); Bernd Abel, Markkleeberg (DE); Ales Charvat, Markkleeberg (DE)

(73) Assignee: Novelis Inc., Atlanta, GA (US)

( * ) Notice: Subject to any disclaimer, the term of this patent is extended or adjusted under 35 U.S.C. 154(b) by 208 days.

(21) Appl. No.: 14/623,181

(22) Filed: Feb. 16, 2015

(65) Prior Publication Data

US 2015/0233870 A1    Aug. 20, 2015

Related U.S. Application Data

(60) Provisional application No. 61/941,404, filed on Feb. 18, 2014.

(51) Int. Cl.
*G01N 29/04* (2006.01)
*G01N 29/24* (2006.01)
*G01N 29/44* (2006.01)

(52) U.S. Cl.
CPC ......... *G01N 29/2418* (2013.01); *G01N 29/04* (2013.01); *G01N 29/44* (2013.01);
(Continued)

(58) Field of Classification Search
CPC .... G01N 29/22; G01N 29/043; G01N 29/221; G01N 29/2418; G01N 21/1702;
(Continued)

(56) References Cited

U.S. PATENT DOCUMENTS

| 3,948,345 A * | 4/1976 | Rosencwaig | G01N 21/1702 356/432 |
| 4,255,971 A * | 3/1981 | Rosencwaig | G01N 21/1702 356/432 |

(Continued)

OTHER PUBLICATIONS

Bell, Alexander Graham, "Upon the production and reproduction of sound by light," American Journal of Sciences, Oct. 1880, pp. 305-324, Series 3, vol. 20 (118), Yale University, New Haven, Connecticut.

(Continued)

*Primary Examiner* — Laura Martin
*Assistant Examiner* — Rose M Miller
(74) *Attorney, Agent, or Firm* — Kilpatrick Townsend & Stockton LLP

(57) ABSTRACT

A measuring device for non-mechanical-contact measurement of a layer, the measuring device including a light source operative to generate a pulse adapted to interact with the layer so as to generate a thermal wave in a gas medium present adjacent the layer. The thermal wave causes an acoustic signal to be generated. The measuring device further includes a detector adapted to detect a first signal responsive to the acoustic signal, the detector not being in mechanical contact with the layer. The first signal is representative of the measured layer.

18 Claims, 17 Drawing Sheets

(52) U.S. Cl.
CPC ............... *G01N 2291/0237* (2013.01); *G01N 2291/02854* (2013.01); *G01N 2291/102* (2013.01); *G01N 2291/103* (2013.01)

(58) Field of Classification Search
CPC ........... G01N 21/1706; G01N 21/1708; G01N 29/04; G01N 29/044; G01N 2291/0237; G01N 2291/02854; G01N 2291/102; G01N 2291/103
USPC .......................................... 73/642, 643, 601
See application file for complete search history.

(56) References Cited

U.S. PATENT DOCUMENTS

| | | | | |
|---|---|---|---|---|
| 4,522,510 | A * | 6/1985 | Rosencwaig | G01B 11/0666 356/43 |
| 4,632,561 | A * | 12/1986 | Rosencwaig | G01N 21/47 356/432 |
| 5,688,049 | A * | 11/1997 | Govorkov | G01N 25/18 374/44 |
| 6,041,020 | A * | 3/2000 | Caron | G01H 9/008 356/340 |
| 2004/0085550 | A1 | 5/2004 | Okuno et al. | |
| 2012/0186348 | A1 | 7/2012 | Matsumoto et al. | |

OTHER PUBLICATIONS

Powell, D. W. and Hill, Trevor, "Non-dispersive infra-red gas analysis in science, medicine, and industry—Chapter 1: Non-Dispersive Infra-Red Gas Analyser Systems," 1968, pp. 1-74, Hilger, United Kingdom.

Powell, D. W. and Hill, Trevor, "Non-dispersive infra-red gas analysis in science, medicine, and industry—Chapter 5: Semiconductor Infra-Red Radiation Detectors," 1968, pp. 149-167, Hilger, United Kingdom.

Kanstad, S. O, et al., "Open membrane spectrophone for photoacoustic spectroscopy," Optics Communications, Sep. 1, 1978, pp. 367-371, vol. 26, No. 3, North-Holland Publishing Co., Amsterdam, Netherlands.

Mandelis, A., et al., "Photoacoustic spectroscopy of thin $SiO_2$ films grown on (100) crystalline Si substrates: A thermal interferometric technique complementary to optical interferometry," Applied Physics A, Jan. 1, 1984, pp. 153-159, vol. 33, Issue 3, Springer-Verlag.

Tam, A. C., "Pulsed-laser generation of ultrashort acoustic pulses: Application for thin-film ultrasonic measurements," Applied Physics Letters, Sep. 1, 1984, pp. 510-512, vol. 45, Issue 5, American Institute of Physics, Melville, New York.

Todorovic, D. M., et al., "Photoacoustic investigation of thermal and transport properties of amorphous GeSe thin films," J. Appl. Phys., Jan. 1, 1994, p. 4012, vol. 76, No. 7, American Institute of Physics, Melville, New York.

Kopylova, D. S., et al., "Thickness measurement for submicron metallic coatings on a transparent substrate by laser optoacoustic technique," Acoustical Physics, Nov. 1, 2008, pp. 783-790, vol. 54, Issue 6, Springer-Verlag.

International Patent Application No. PCT/US2015/016033, International Search Report and Written Opinion mailed Apr. 30, 2015, 10 pages.

International Patent Application No. PCT/US2015/016033, International Preliminary Report on Patentability mailed Sep. 1, 2016, 8 pages.

Canadian Patent Application No. 2,939,534, Office Action dated May 4, 2017, 3 pages.

* cited by examiner

PHOTO-ACOUSTIC DEVICE AND METHOD FOR NON-CONTACT MEASUREMENT OF THIN LAYERS

CROSS-REFERENCE TO RELATED APPLICATIONS

This application claims priority, under 35 U.S.C. §119(e), from U.S. Provisional Application No. 61/941,404, filed on Feb. 18, 2014, entitled "PHOTO-ACOUSTIC DEVICE AND METHOD FOR NON-CONTACT MEASUREMENT OF THIN LAYERS," the contents of which is incorporated herein by reference in its entirety.

FIELD OF THE INVENTION

The present invention relates generally to a device and method for the measurement of a layer and in particular to a photo-acoustic device and measuring method for non-mechanical-contact measurement of thin layer coatings.

BACKGROUND

The terms thin films or thin layers, refer to layers in the micrometer (μm) and/or nanometer (nm) thickness range. The manufacturing of thin layers is relevant in industrial production processes, for example to apply functional layers with fine-tuned properties while saving expensive raw materials. Such thin films have a variety of applications in optics, microelectronics and the treatment of surfaces. A uniform thickness and well-defined characterization of the layer is a challenge for the manufacturer.

For example, to improve the corrosion resistance and the adhesion of lacquers, seals and adhesives on aluminum strips, a conversion coating may be applied through a process called coil-coating. Previously, these conversion coatings contained chemical components with chromium as an ingredient; however, industry is moving to use chromium-free based conversion coatings. During production it may be necessary to monitor the quality of the applied conversion coating and/or their chemical composition, in particular the amount of key ingredients in real-time. However, in a coil-coating process, the aluminum strip may move with a speed up to several hundred meters per minute through the production machinery.

Certain techniques are known to analyze these kinds of thin layers. All of them share the problem that they are not able to analyze fast-moving samples and nanometer thick layers which are applied on rough surfaces. White light interferometry requires at least a film thickness that is within the range of the wavelength of visible light while the normal thickness of a conversion coating is below 100 nanometers. Photometry also requires thicker layers to obtain the desired sensitivity. X-Ray-fluorescence (online-XRF) may be too slow and, like Beta Backscatter, requires radiation shielding that would be costly in an industrial environment. Since the roughness of a typical aluminum strip surface is in the micrometer range, it is difficult to use ellipsometry, which requires very flat surfaces like in the semiconductor industry. During the coil-coating process, the aluminum strip will move fast and vibrate, which rules out attenuated total reflection (ATR) spectroscopy, which needs a distance to the samples surface smaller than the wavelength used.

Further, the photo-acoustic (hereinafter also referred to as PA) techniques based on the PA principle are known to measure film layers in which a sample is exposed to electromagnetic radiation. The absorption of the radiation leads to a higher temperature in the sample and volume change, which is followed by a dilation of the sample surface. In-turn, the surface dilation causes an impulse or periodic changes of the surrounding medium density, which may be detected with a microphone as sound. The sensitivity to sample ingredients using the photo-acoustic technique may be better than conventional light based spectroscopy. However, in known PA techniques, the sample thickness has not been smaller than about 12 micrometers and the microphone is placed in mechanical contact with (i.e. touching) the sample or requires a liquid medium in contact with the sample to transmit sound to the microphone, which may be unsuitable for measuring conversion coatings below 100 nanometers in the coil-coating manufacturing process.

Therefore, a fast, real-time, nondestructive and non-mechanical-contact measurement technique for conversion layers that is insensitive to noise, dirt and shocks suitable for use in the coil coating manufacturing process is desired.

SUMMARY

According to one embodiment of the present invention, a measuring device for non-mechanical-contact measurement of a layer is presented. The measuring device includes a light source operative to generate a pulse adapted to interact with the layer so as to generate a thermal wave in a gas medium present adjacent the layer. The thermal wave causes an acoustic signal to be generated. The measuring device further includes a detector adapted to detect a first signal responsive to the acoustic signal. The detector is not in mechanical contact with the layer. The first signal is representative of the measured layer.

According to one embodiment, the pulse is adapted to interact with the layer without permanently altering the layer. According to one embodiment, a wavelength of the pulse is associated with a penetration depth of the pulse in the layer. According to one embodiment, the pulse wavelength is preferably selected to be in the range from about 150 to about 500 nanometers, more preferably in the range from about 180 to about 350 nanometers, most preferably about 213 nanometers. The penetration depth is greater than a thickness of the layer. According to one embodiment, a temporal width of the pulse is associated with a thermal diffusion length of the layer. The thermal diffusion length is substantially equal to a thickness of the layer. According to one embodiment, the pulse width is preferably selected to be in the range of about 50 picoseconds (psec) to about 100 nanoseconds (nsec), more preferably in the range from about 1 nsec to about 50 nsec.

According to one embodiment, the pulse is associated with an absorption of the pulse within the layer. The absorption is substantially greater than an absorption of the pulse within a substrate in mechanical contact with the layer. The layer is disposed between the substrate and the gas medium.

According to one embodiment, a thickness of the layer is less than 100 nm. According to one embodiment, the layer is selected from the group consisting of a solid, a gel, a liquid, and a powder.

According to one embodiment, the detector includes a transducer adapted to have a frequency response greater than a frequency range of a noise ambient in the vicinity of the detector and to generate the first signal. According to one embodiment, the frequency response of the transducer is above 200 kilohertz.

According to one embodiment, the detector includes a sound coupler adapted to direct a portion of the acoustic signal to the detector. According to one embodiment, the sound coupler includes a cylindrical hollow body including an opening disposed proximal to the detector. According to one embodiment, the sound coupler includes a longitudinal axis oriented in a first direction intersecting with a region where the pulse interacts with the layer. According to one embodiment, the sound coupler is further adapted to reject a portion of ambient acoustic noise originating from a second direction other than the first direction.

According to one embodiment, the measuring device further includes a signal processor adapted to improve a signal to noise ratio of the first signal to form a second signal, and calculate a distance between the detector and a region of the gas medium generating the thermal wave. The signal processor is further adapted to compensate the second signal in accordance with the distance to produce a third signal that is substantially independent of a fluctuation of the distance, and determine a measurement responsive to a composition and thickness of the film in accordance with an amplitude of the third signal and a predetermined look-up table.

According to one embodiment, the signal processor includes a filter adapted to selectively pass a high frequency portion of the first signal to form the second signal. According to one embodiment, the filter includes a quality factor greater than ten at 3 decibels below a peak amplitude of the first signal at a resonant frequency of the filter.

According to one embodiment, the signal processor is further adapted to calculate the distance in accordance with a speed of the acoustic signal in the gas medium multiplied by a time of flight of the acoustic signal. According to one embodiment, the signal processor is further adapted to determine the time of flight by subtracting a time associated with generating the pulse from a time associated with receiving the acoustic signal at the detector.

According to one embodiment, the measuring device further includes a measuring head including an exit port where the pulse exits the measuring head into the gas medium. The detector and the exit port are each rigidly attached to the measuring head. According to one embodiment, the measurement head is adapted to move in a direction substantially parallel to a surface of the layer. According to one embodiment, the exit port is coupled to the light source via an optical fiber.

According to one embodiment, the light source is further operative to generate a multitude of pulses each having different associated characteristics selected to interact with a multitude of different associated constituents of the layer. The measuring device includes a multitude of different detectors each associated with a different one of the multitude of pulses.

According to one embodiment, the measuring device further includes an energy detector adapted to measure an energy of the pulse. According to one embodiment, the measuring device further includes a signal processor adapted to compensate the first signal in accordance with the energy to form a second signal that is substantially independent of a fluctuation of the energy.

According to one embodiment, the layer is a coating applied in a coil-coating or a roll-to-roll coating process and the first signal is detected in real time as the layer moves in relation to the measuring device. According to one embodiment, the layer is a conversion coating applied on an aluminum substrate and the layer includes silicon (Si) and/or a metal selected from the group consisting of zirconium (Zr), titanium (Ti), and chromium (Cr).

According to one embodiment of the present invention, a method for non-mechanical-contact measurement of a layer is presented. The method includes generating a pulse adapted to interact with the layer to generate a thermal wave in a gas medium present adjacent the layer, thereby causing an acoustic signal to be generated. The method further includes detecting a first signal responsive to the acoustic signal without mechanically contacting the layer. The first signal is representative of the measured layer.

According to one embodiment, the method further includes selecting the layer from the group consisting of a solid, a gel, a liquid, and a powder. According to one embodiment, the method further includes generating the first signal using a transducer having a frequency response greater than a frequency range of a noise ambient in the vicinity of the detector. According to one embodiment, the method further includes directing a portion of the acoustic signal to a detector.

According to one embodiment, the method further includes using a sound coupler having a cylindrical hollow body including an opening disposed proximal to the detector. According to one embodiment, the method further includes orienting a longitudinal axis of the sound coupler in a first direction that intersects with a region where the pulse interacts with the layer. According to one embodiment, the method further includes rejecting a portion of ambient acoustic noise originating from a second direction other than the first direction using the sound coupler.

According to one embodiment, the method further includes improving a signal to noise ratio of the first signal to form a second signal, and calculating a distance between a detector and a region of the gas medium generating the thermal wave. The method further includes compensating the second signal in accordance with the distance to produce a third signal that is substantially independent of a fluctuation of the distance, and determining a measurement responsive to a composition and thickness of the film in accordance with an amplitude of the third signal and a predetermined look-up table.

According to one embodiment, the method further includes selectively passing a high frequency portion of the first signal to form the second signal. According to one embodiment, the method further includes using a filter including a quality factor greater than ten at 3 decibels below a peak amplitude of the first signal at a resonant frequency of the filter.

According to one embodiment, the method further includes calculating the distance in accordance with a speed of the acoustic signal in the gas medium multiplied by a time of flight of the acoustic signal. According to one embodiment, the method further includes determining the time of flight by subtracting a time associated with generating the pulse from a time associated with receiving the acoustic signal at the detector.

According to one embodiment, the method further includes providing a measuring head including an exit port where the pulse exits the measuring head into the gas medium, and rigidly attaching to the measuring head the detector and the exit port. According to one embodiment, the method further includes moving the measurement head in a direction substantially parallel to a surface of the layer. According to one embodiment, the method further includes coupling the exit port to the light source via an optical fiber.

According to one embodiment, the method further includes generating a multitude of pulses each having different associated characteristics selected to interact with a multitude of different associated constituents of the layer, and using a multitude of different detectors each associated with a different one of the multitude of pulses.

According to one embodiment, the method further includes measuring an energy of the pulse. According to one embodiment, the method further includes compensating the first signal in accordance with the energy to form a second signal that is substantially independent of a fluctuation of the energy. According to one embodiment, the method further includes applying the layer as a coating in a coil-coating or a roll-to-roll coating process, and detecting the first signal in real time as the layer moves in relation to the measuring device.

A better understanding of the nature and advantages of the embodiments of the present invention may be gained with reference to the following detailed description and the accompanying drawings.

DETAILED DESCRIPTION

Figure 1:
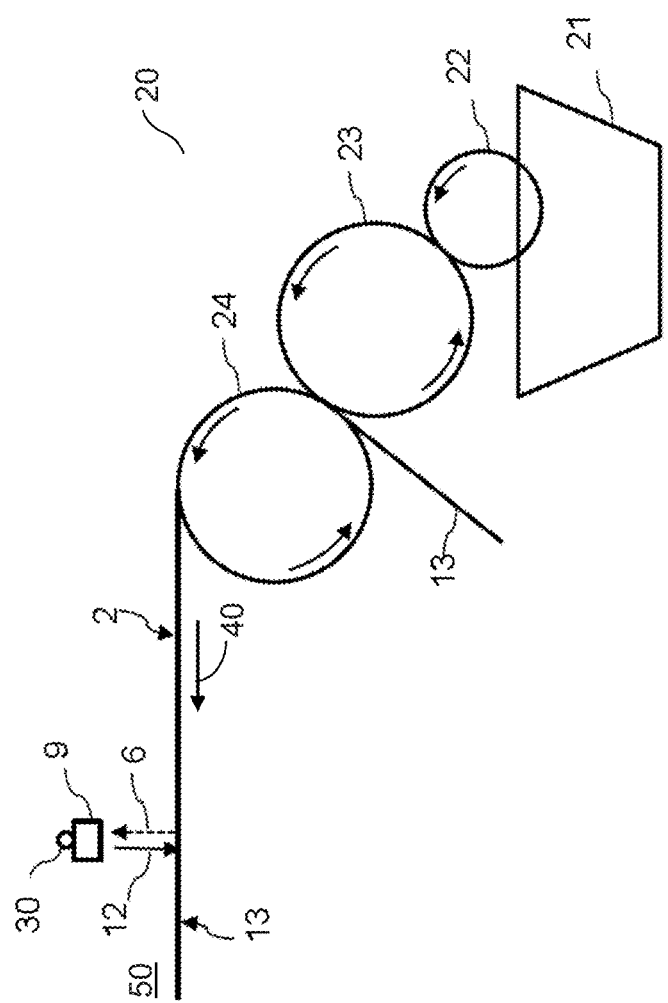
FIG. 1 depicts a simplified schematic side view of a photo-acoustic measuring head for use in a coil coating process, in accordance with one embodiment of the present invention.

FIG. 1 depicts a simplified schematic side view 20 of a photo-acoustic measuring head 9 for use in a coil coating process, in accordance with one embodiment of the present invention. A measuring device for non-mechanical-contact measurement of a layer, hereinafter also referred to as a sample layer, is presented, which uses the photo-acoustic effect to enable on-line quality sampling of fast moving samples of thin films in the nanometer range in real-time during an industrial coating process. A part of the measuring device may include a measuring head 9. The measuring device may include a light source (not shown) operative to generate a pulse 12 of light and/or electromagnetic energy adapted to interact with sample layer 2 so as to generate a thermal wave (not shown) in a gas medium 50 present adjacent layer 2 near an interface between layer 2 and gas medium 50 without permanently altering layer 2 when the measuring device is invoked to measure the layer. The thermal wave causes an acoustic signal 6 to be generated. The measuring device further includes a detector (not shown) in measuring head 9 adapted to detect a first signal responsive to acoustic signal 6. The first signal may be representative of a characteristic of the measured layer 2, such as for example a thickness and/or the amount of a material constituent of layer 2. The detector is not in mechanical contact with layer 2. In one embodiment, gas medium 50 may be air or any suitable gas ambient tailored for the manufacturing process.

In one embodiment, layer 2 may be a conversion coating applied on a moving aluminum strip 13, hereinafter also referred to as a substrate, during a coil-coating or roll-to-roll manufacturing process. In one embodiment layer 2 may include silicon (Si), and/or a metal as a constituent such as zirconium (Zr), titanium (Ti), and/or chromium (Cr). A portion of the coil-coating process machinery may include three rollers. A metering roller 22 picks up a water-based acidic solution from a bath 21. The liquid solution on the metering roller is transferred to an application roller 23, which in-turn transfers the liquid through a small gap between aluminum strip 13 and application roller 23. Aluminum strip 13 may be wound partly around aluminum transporting support roller 24, which moves the aluminum strip. The rollers move in the directions as indicated by the curved arrows to coat the aluminum strip as it moves through the assembly of rollers.

After leaving transporting support roller 24, aluminum strip 13 may be covered with a liquid film solution that may have a thickness up to 20 μm applied with a process speed up to several hundred meters per minute as aluminum strip 13 moves off transporting support roller 24 in a direction indicated by arrow 40. After a drying process, the liquid film solution dries resulting in layer 2, which may have a thickness in a range from 20 to 70 nm. In one embodiment, layer 2 may be in the form of a solid, liquid, gel, or a powder.

In one embodiment, measurement head 9 may be mounted within a distance around 40 millimeter (mm) away from the moving strip such that the measurement head 9 is not in mechanical contact with the fast moving layer 2, but is instead separated from layer 2 by gas medium 50, which transmits pulse 12 and acoustic signal 6 as described below. In one embodiment, measurement head 9 may be adapted to move in a direction substantially parallel to a surface of the layer, e.g. in a direction of the film motion and/or in a direction into the figure. Accordingly, measurement head 9 may be mounted on a first linear motion control unit 30 having a longitudinal axis that may be perpendicular to the moving direction of the aluminum strip and parallel to the rotation axis of the rollers. Moving the measurement head provides the ability to measure, for example, the thickness of the thin layer over the sample width. Two dimensional surface mapping in the plane of the thin film may be provided by a second linear motion control unit (not shown) that moves the longitudinal axis of first linear motion control unit 30 parallel to the direction of thin layer motion. Motion control of measurement head 9 may not be critical because the PA system automatically compensates for variations between the measurement head and the thin layer surface as described below.

Figure 2A:
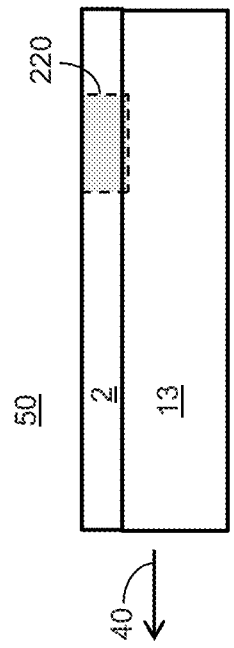
FIG. 2A depicts exposing an exemplary moving layer with a light pulse that penetrates the layer forming an irradiated region of the layer, in accordance with one embodiment of the present invention.

FIGS. 2A-2D depict simplified steps in generating a photo-acoustic signal, in accordance with one embodiment of the present invention. FIG. 2A depicts exposing exemplary moving layer 2 with pulse 12 that penetrates layer 2 forming an irradiated region of the layer, in accordance with one embodiment of the present invention. Layer 2 is overlaying aluminum strip 13, both of which are moving in a direction indicated by arrow 40 during the coil coating process.

Figure 2B:
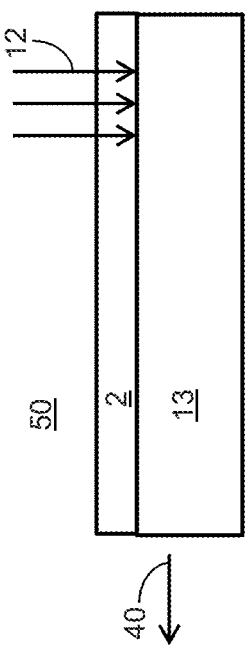
FIG. 2B depicts energy from the light pulse being optically absorbed and thermally diffusing from the irradiated region of the layer depicted in FIG. 2A, in accordance with one embodiment of the present invention.

FIG. 2B depicts energy from pulse 12 being optically absorbed and thermally diffusing in a region 220 from the irradiated region of the layer depicted in FIG. 2A, in accordance with one embodiment of the present invention. It has been found through computer models of the PA technique that for thin films having thickness below 100 nm, the volumetric change in the film due to heating from the pulse as described in prior PA techniques does not produce an acoustic signal of sufficient magnitude to detect in the noise ambient commonly encountered in the coil coating process.

Figure 2C:
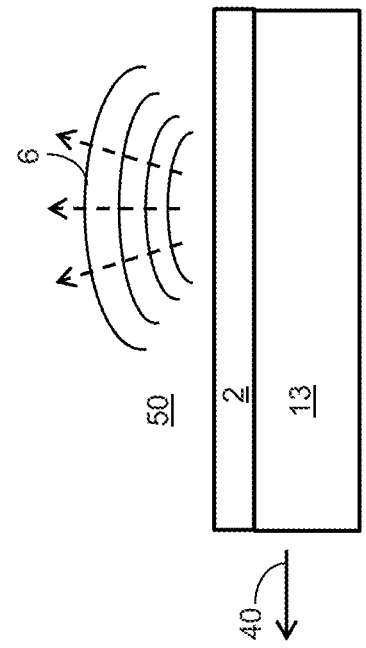
FIG. 2C depicts energy from the irradiated region depicted in FIG. 2B forming a thermal wave in a gas medium at an interface between the thin layer and the gas medium, in accordance with one embodiment of the present invention.

FIG. 2C depicts energy from the irradiated region depicted in FIG. 2B forming a thermal wave 230 in gas medium 50 at an interface between thin layer 2 and gas medium 50, in accordance with one embodiment of the present invention. Rather than changing the volume of film 2 substantially, the thermal energy in the irradiated region of the film heats the gas medium 50 at the interface between thin layer 2 and gas medium 50. The heated gas medium then expands quickly forming a thermal wave 230 in the region depicted by the dashed line.

Figure 2D:
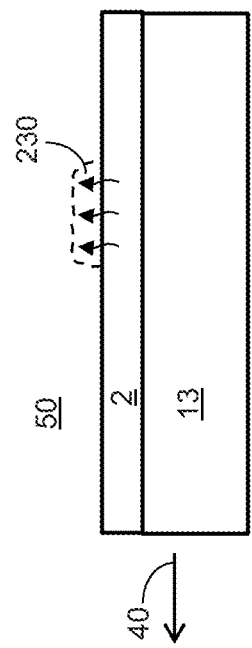
FIG. 2D depicts energy from the thermal wave depicted in FIG. 2C generating an acoustic signal, in accordance with one embodiment of the present invention.

FIG. 2D depicts energy from thermal wave 230 depicted in FIG. 2C generating an associated acoustic signal 6, in accordance with one embodiment of the present invention. The heating and subsequent cooling of gas medium 50 triggered by thermal wave 230 at the interface between thin layer 2 and gas medium 50 occurs rapidly. The respective rapid gas volume expansion and contraction generates an ultrasonic acoustic signal 6 that radiates outward from the irradiated film surface through gas medium 50 as indicated by the dashed arrows carrying information related to the thickness and composition of thin layer 2. The speed of the PA processes depicted in FIGS. 2A-2D, excluding time of flight of the acoustic signal, take place within several tens of microseconds.

Figure 3:
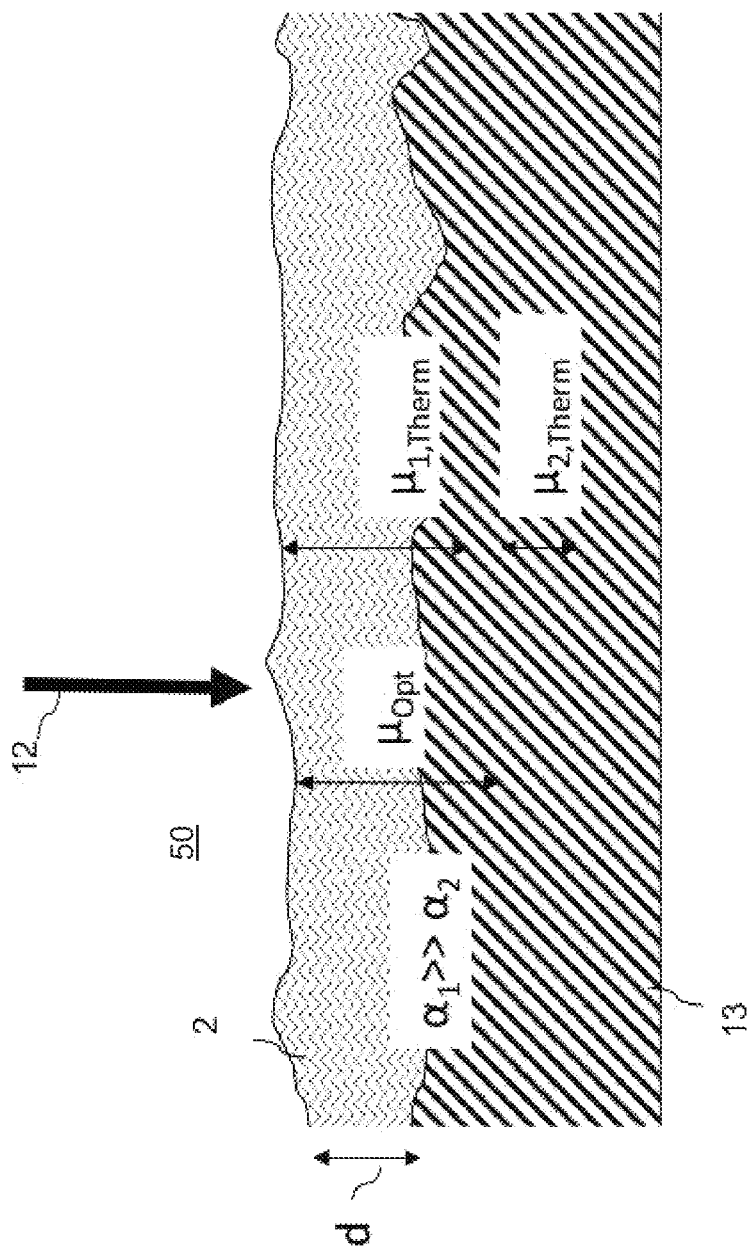
FIG. 3 depicts the selection of characteristics for the light pulse in order to match to characteristics of the thin layer and its supporting aluminum strip or substrate, in accordance with one embodiment of the present invention.

FIG. 3 depicts the selection of characteristics for light pulse 12 in order to match to characteristics of thin layer 2 and its supporting aluminum strip 13 or substrate, in accordance with one embodiment of the present invention. The conversion coating or layer 2 is depicted under high magnification and includes a thickness, d, which is applied on the rough surface of aluminum strip 13. The typical roughness of a non-polished industrial aluminum surfaces is in a range from 0.2 to 1 μm. Layer 2 may be disposed between the substrate and gas medium 50.

It is emphasized that the methods and apparatus of the PA technique to measure films with thickness d less than 100 nm in the coil coating industrial environment, as described by embodiments of the present invention, are significantly different than those previously described such as, for example, those known PA techniques to measure films with thickness much greater than 100 nm in a laboratory setting. Accordingly, characteristics of the light pulse may be specially selected to meet at least one of the following three pulse characteristics to increase the generated acoustic signal and the information associated with layer 2 contained therein. Further, embodiments of the present invention are not limited to the moving metal coil coating process described herein, but may be used, for example, in characterizing or measuring the application of pretreatments, lubricants, and/or adhesives in various industries, such as for example, the automotive industry, and including measurements on stationary target layers that are in the thickness range below about 100 nm.

In one embodiment, a wavelength of pulse 12 may be selected such that a penetration depth, $\mu_{opt}$, of the pulse in layer 2 is greater than thickness d. Selecting $\mu_{opt} > d$ has the advantage, that the resulting acoustical signal may contain information associated with the substrate to conversion layer boundary, which may be used for better measurement characterization of layer thickness d. In one embodiment, the pulse wavelength is preferably selected to be in the range from about 150 to about 500 nanometers, more preferably in the range from about 180 to about 350 nanometers, and/or most preferably about 213 nanometers, which includes the ultraviolet (UV) to visual spectral range.

In another embodiment, a temporal width of pulse 12, e.g. the pulse length in time, may be selected such that a thermal diffusion length $\mu_{1therm}$ of layer 2 is substantially equal to a thickness, d, of layer 2. Selecting $\mu_{1therm} \sim d$ helps prevent heat drainage into the substrate, which may adversely affect the acoustic signal excitation. Instead, heat energy may be directed into the gas ambient via the thermal wave to help generate the desired acoustic signal as previously explained. In one embodiment, pulsed light sources with a temporal pulse width may be preferably selected to be in the range of about 50 picoseconds (psec) to about 100 nanoseconds (nsec), more preferably in the range from about 1 nsec to about 50 nsec.

In one embodiment, pulse 12 is selected such that an optical absorption, $\alpha_1$, of pulse 12 within layer 2 may be substantially greater than an optical absorption, $\alpha_2$, of the pulse within a substrate, e.g. aluminum strip 13, that may be in mechanical contact with and supporting layer 2. In other words, $\alpha_1 \gg \alpha_2$. Selecting $\alpha_1 \gg \alpha_2$ ensures that the wavelength of the pulse is selected to favor absorption in layer 2 rather than in the substrate, again to improve acoustic signal generation. A strong acoustic signal is easier to detect and weak signals from the substrate may be neglected.

Figure 4:
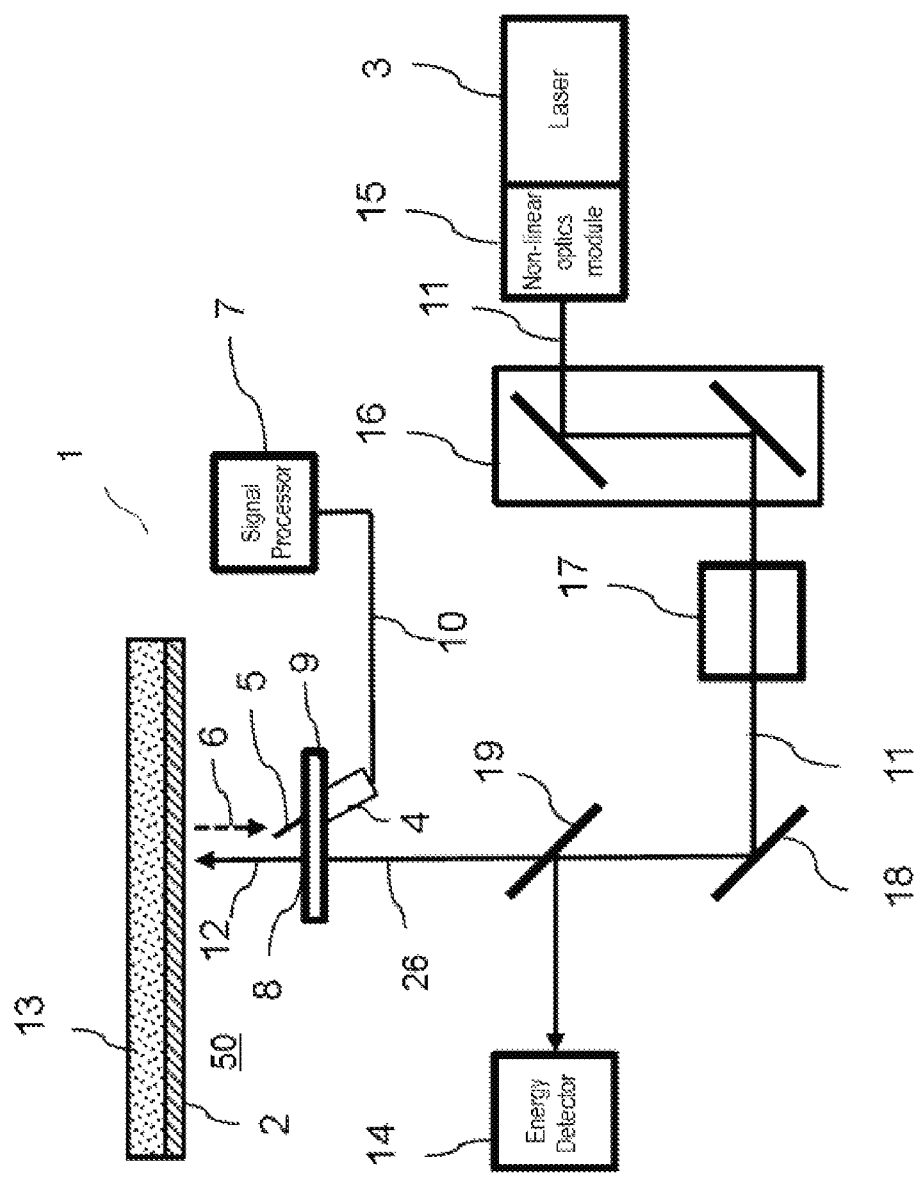
FIG. 4 depicts a simplified schematic block diagram of the non-mechanical-contact photo-acoustic measuring system, in accordance with one embodiment of the present invention.

FIG. 4 depicts a schematic block diagram of the non-mechanical-contact PA measuring system 1, also referred to herein as the PA system, in accordance with one embodiment of the present invention. PA system 1 includes a pulsed laser 3, a non-linear optics module 15, an optical filter component 16, a variable attenuator 17, a mirror 18, a beam splitter 19, and an energy detector 14. Pulsed laser 3 generates pulse 12 and may include, for example a neodymium-doped yttrium-aluminum-garnet (Nd:YAG) laser module, which may be pumped by a flash lamp. In one embodiment, the source of the pulse may be a supercontinuum laser and/or an optical parametric oscillator (OPO).

In one embodiment, the excitation energy of pulse 12 may be selected such that an acoustic signal is generated which is strong enough to be detected with a sufficiently high signal-to-noise ratio to reliably obtain data associated with characteristics of layer 2. In other words, the acoustic signal may be representative of a characteristic of the measured layer including data, such as for example the thickness of the layer and/or the amount of a material constituent of the layer. On the other hand, the excitation energy is selected low enough such that non-linear processes and ablation of layer 2 are avoided. If the excitation energy is too high, the signal amplitude may not correlate linearly with the thickness of layer 2, and/or pulse 12 may even damage layer 2.

Non-linear optics module 15 fed by laser 3 generates UV light beam 11 by converting the laser's wavelength 1064 nm into its 5th harmonic, 213 nm, which is filtered by optical filter component 16 to block undesired wavelengths by reflection angles under 45 degrees. The energy of the filtered light may be reduced as needed by attenuator 17. UV light beam 11 is reflected by mirror 18 into beam splitter 19, which distributes approximately two-thirds of the energy into energy detector 14 and forwards approximately one-third of the energy towards the sample layer. Energy detector 14 may be adapted to measure the energy of the pulse and couples feedback control signals (not shown) to attenuator 17 such that the energy of each pulse may be kept uniform as described below. The energy and pulse length of the emitted pulse 12 provides for the non-destructive measurement of layer 2 by preventing ablation or photochemistry in layer 2. Laser 3, non-linear optics module 15, optical filter component 16, variable attenuator 17, mirror 18, beam splitter 19, and energy detector 14 may be included in an optical subsection, which may be housed separately from other parts of PA system 1.

PA system 1 further includes measurement head 9 and detector 4, 5. Measurement head 9 may include detector 4, 5, and a light exit port 8, where pulse 12 may exit measuring head 9 into gas medium 50. Detector 4, 5 and exit port 8 may be each rigidly attached to measuring head 9, which provides an advantage that the relative distance between the detector and light exit port is not influenced by shocks or vibrations so that the distance between the detector and the irradiated layer 2 sample surface may be accurately determined via a time of flight of acoustic signal 6 as described below.

Measurement head 9 may be flexibly attached to the optical subsection via a flexible optical fiber cable 26, which may be coupled between exit port 8 and beam splitter 19. Measurement head 9, which takes little space compared to the optical subsection, may thus be more easily handled and flexibly positioned in close proximity to but not in mechanical contact with layer 2 on aluminum strip 13, both of which are moving rapidly past PA system 1, without significant modification to the coil coating process set-up. Therefore, the optical subsection may be located farther away from or remote to the moving strip to advantageously protect the optical components from vibration and dust contamination caused by the coil coating process. The resulting system with measuring head separated from the optical subsection provides better safety and maintenance requirements for industrial application than if the measurement head and optical section were in the same system enclosure in proximity to the moving aluminum strip.

Pulse 12 may leave exit port 8, which may include a terminated end of optical fiber cable 26, and be transmitted through gas medium 50 towards layer 2 and directed, in one embodiment, substantially orthogonally to the surface of layer 2. In one embodiment, pulse 12 is directed substantially orthogonally but not exactly orthogonally to prevent unwanted reflection of pulse 12 back into the optical subsection, which may degrade components in the optical subsection over time. Accordingly, the angle of pulse 12 relative the surface of layer 2 may be in the range of less than 90 degrees but more than 80 degrees, for example preferably in the range of 89 to 86 degrees.

In one embodiment, Pulse 12 may leave measurement head 9 unfocused. In another embodiment, Pulse 12 may be focused onto layer 2. After pulse 12 leaves exit port 8, a region of layer 2 may be irradiated so as to produce acoustic signal 6 via a thermal wave as described above. Acoustic signal 6 then propagates from the thermal wave-generating region where layer 2 was irradiated through gas medium 50 towards detector 4, 5. Therefore, because measurement head 9 may be separated from layer 2 by gas medium 50, PA system 1 provides non-mechanical-contact measurement of layer 2. Further, acoustic signal 6 may be detected in real time as layer 2 moves in relation to PA system 1 because the speed of the measurement is fast compared to the movement of layer 2 in the coil-coating process.

PA system 1 further includes signal processor 7, which may be coupled to detector 4, 5 by flexible cable 10, and understood to be coupled to laser 3, attenuator 17, and energy detector 14 for communication and/or control functions, which coupling signals are not shown to better explain the embodiments of the invention. Signal processor 7, may include control electronics, a computer processor, and non-transient memory adapted to store program code to control functions of PA system 1, which are described below.

Figure 15:
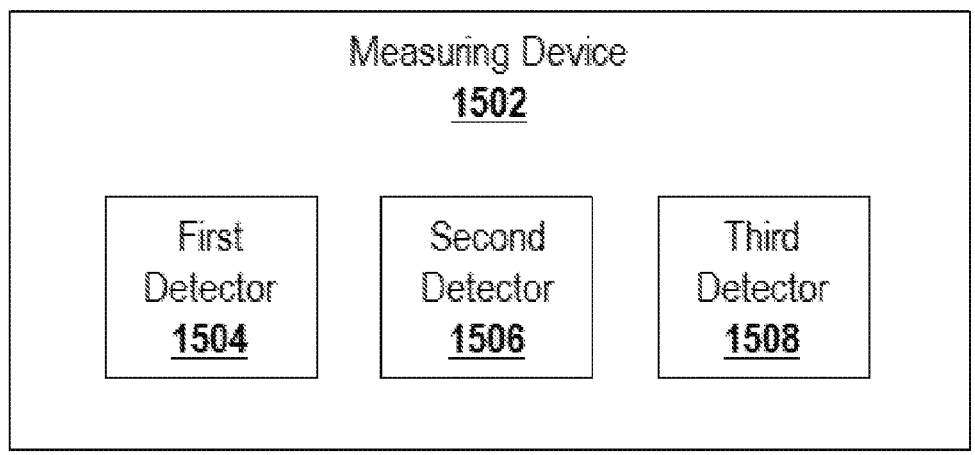
FIG. 15 depicts a measuring device including a multitude of different detectors.

In one embodiment, the optical subsection is further operative to generate a multitude of pulses each having different associated characteristics selected to interact with a multitude of different associated constituents of layer 2. A measuring device may include a multitude of different detectors each associated with a different one of the multitude of pulses, as depicted in FIG. 15. For example layer 2 may include a zirconium containing active compound inside an organic binder. One pulse may be selected to include characteristics tuned to generate an acoustic wave responsive to the amount of zirconium containing active compound, while another pulse may be selected to include characteristics tuned to generate an acoustic wave responsive to the amount of organic binder in layer 2. The two different pulses may differ in wavelength, energy, and/or temporal pulse length to monitor both the zirconium containing active compound and the organic binder in real time.

In one embodiment, PA system 1 may include a multitude of different laser sources each having different tuned characteristics. In another embodiment, PA system 1 may include a spectrally broadband laser optically processed to generate the multitude of pulses at different wavelengths. In one embodiment, PA system 1 may include a multitude of measurement heads each adapted to sample a multitude of different regions on layer 2. For example, thickness and/or concentration of constituents of layer 2 across the entire width on the aluminum strip 13 may be measured simultaneously in real-time.

The embodiments described herein provide a way to do complex spectroscopic investigations. For example, the chosen multitude of wavelengths may individually target a multitude of different associated molecules embedded in a matrix in layer 2 enabling measuring their concentrations independent from each other, resulting in multiple chemical information like reaction kinetics in layer 2.

Figure 5:
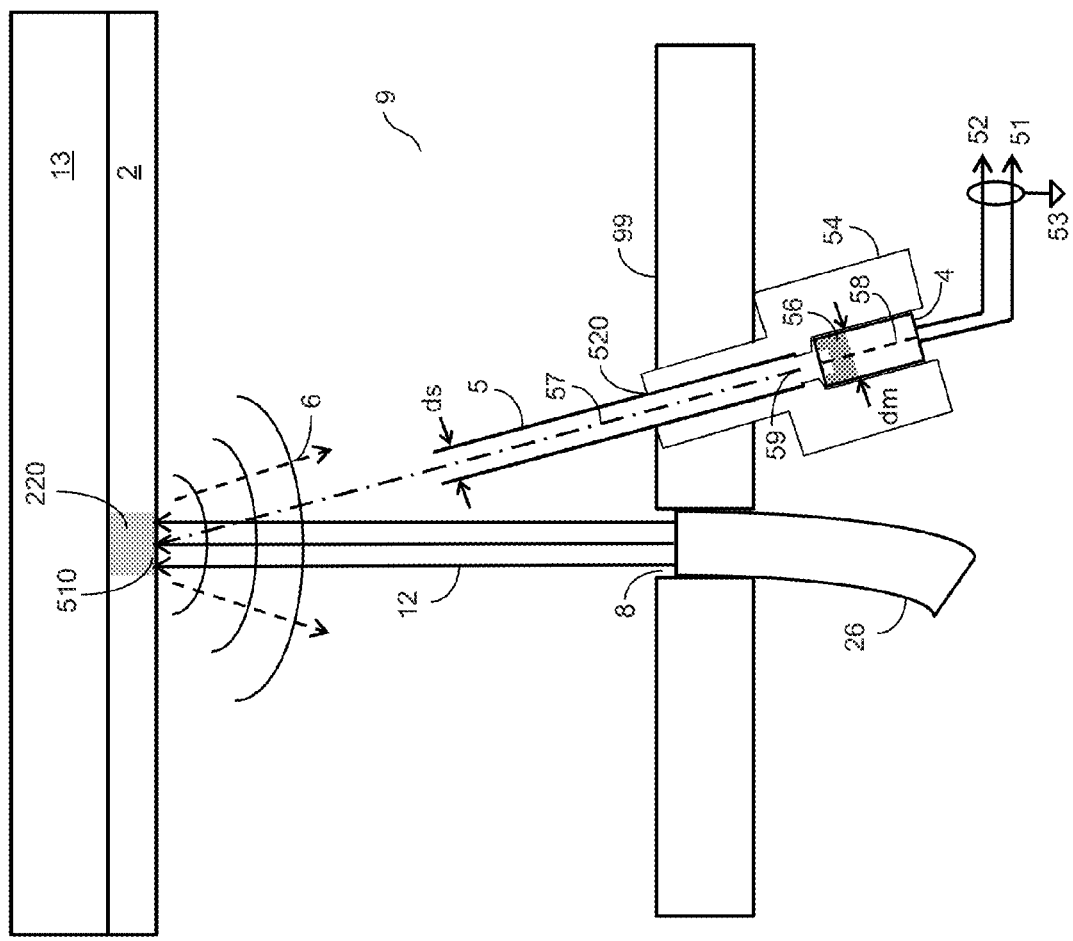
FIG. 5 depicts a simplified schematic block diagram of the measuring head depicted in FIG. 4, in accordance with one embodiment of the present invention.

FIG. 5 depicts a schematic block diagram of measuring head 9 depicted in FIG. 4, in accordance with one embodiment of the present invention. Measuring head 9 may include detector 4, 5, and a mounting bracket 99. Mounting bracket 99 may include a housing 54, and exit port 8. Housing 54 may include detector 4, 5, which in-turn may include a microphone 4 and a sound coupler 5. In one embodiment, microphone 4 may be adapted to include a transducer 56, which in—turn may be adapted to have a frequency response greater than a frequency range of a noise ambient in the vicinity of the detector and to generate the first electrical signal associated with a high frequency portion of acoustic signal 6 to further improve the signal-to-noise ratio of the PA system as described below.

In one embodiment, sound coupler 5 may be adapted to direct a high frequency portion of acoustic signal 6 to transducer 56 of microphone 4 of detector 4,5. In one embodiment, sound coupler 5 may include a cylindrical hollow body including two openings at opposite ends of the cylindrical hollow body. One opening 59 of coupler 5 may be disposed proximal to transducer 56 of microphone 4 of detector 4, 5. In one embodiment, the sound coupler 5 may include an outer diameter, ds, being about equal to a diameter, dm, of transducer 56. In one embodiment, sound coupler 5 may further include a longitudinal axis 57 oriented substantially in line with a longitudinal axis 58 of microphone 4. In one embodiment, longitudinal axis 58 of microphone 4 may form an angle less than 90 degrees with respect to the surface of layer 2. In one embodiment, the longitudinal axis 57 of sound coupler 5 may be oriented in a first direction so as to intersect substantially at a region 510 on the surface of region 220 of layer 2, where pulse 12 interacts with layer 2, so as to direct acoustic signal 6 from the thermal wave to microphone 4, while rejecting a portion of ambient acoustic noise generated from a second direction other than the first direction in the industrial environment. The rejection of noise in the second direction by sound coupler 5 may be another component for improving the signal-to-noise ratio of the PA system. In one embodiment, sound coupler 5 may be formed of a stainless steel tube about 40 mm long having an outer diameter of about 3 mm and a wall thickness of about 0.2 mm.

The noise rejection may be further accomplished by directly attaching sound coupler 5 through an orifice 520 in housing 54 such that housing 54 and mounting bracket 99 may act as an acoustic shield that further reduces the ambient noise reaching microphone 4, while directing high frequency acoustic signal 6 towards microphone 4. In one embodiment, sound coupler 5 may be attached to housing 54 and oriented in the first direction by inserting about half of sound coupler 5 into orifice 520. In one embodiment, microphone 4 may be directly attached to housing 54 such that the only opening for acoustic waves to enter microphone 4 is through orifice 520 in housing 54 and via sound coupler 5. Further, sound coupler 5 may provide the added benefit of protecting microphone 4 from mechanical stress or damage.

Mounting bracket 99 may include orifice 8 for attaching terminated optical fiber 26 that directs pulse 12 as a beam towards layer 2. Mounting bracket 99 may further include an angled mounting hole adapted to hold housing 54 at the desired orientation. The electrical signal corresponding to acoustic signal 6 may be transmitted via shielded cable having terminals 51-53, where terminal 53 may be the grounded cable shield. Mounting bracket 99 may further include holes or slots (not shown) for securely mounting measuring head 9 at a safe fixed distance from the moving metal coil 2, 13.

Figure 6:
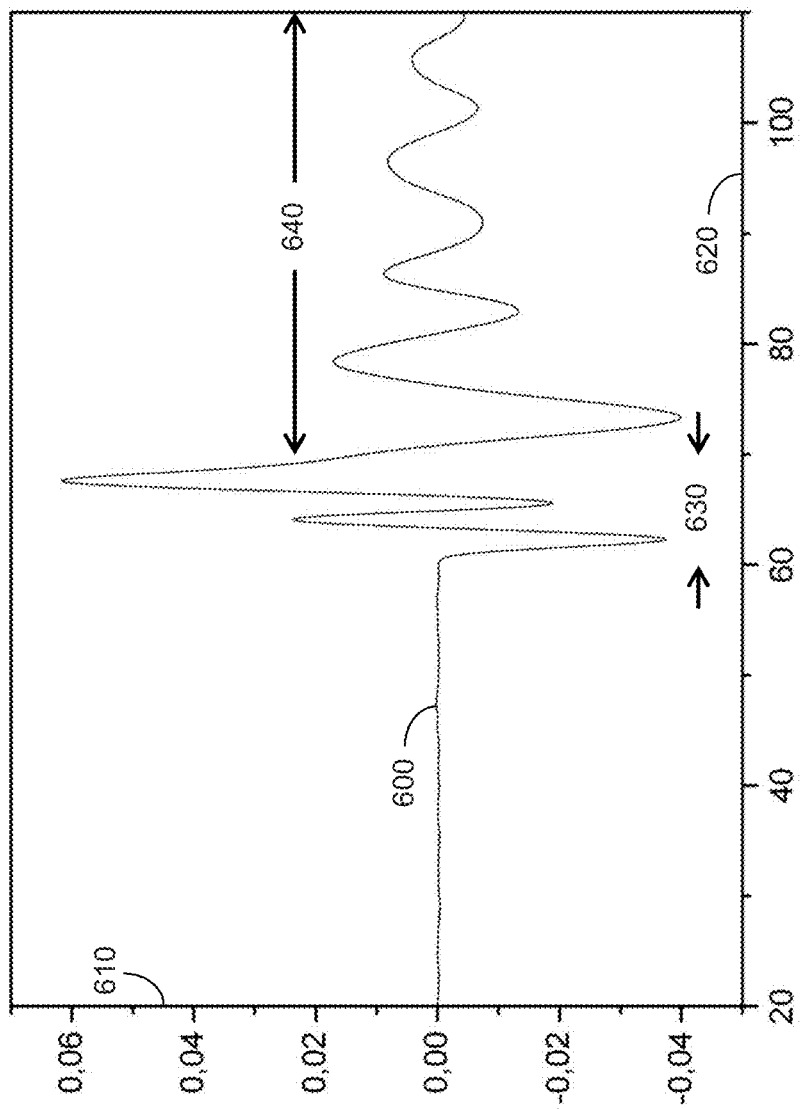
FIG. 6 depicts a raw electrical measurement signal in the time domain from the detector depicted in FIG. 4.

FIG. 6 depicts a raw electrical measurement signal 600 in the time domain from detector 4, 5 depicted in FIG. 4 acquired in a quiet laboratory environment. The vertical axis 610 of FIG. 6 represents the raw electrical measurement signal amplitude in volts (V) from −0.05 to 0.07 V, while the horizontal axis 620 represents elapsed time in microseconds (μs) from 20 to 110 μs. The transducer that responds to acoustic signal 6 may have a frequency response range for directly converting high frequency acoustic signals coupled in air from the interaction of pulse 12 and layer 2 into the raw, i.e. unfiltered, electrical measurement signal. In one embodiment, the transducer may be adapted to respond at a higher frequency than the ambient noise frequency in the industrial environment. The response from the transducer may generate the electrical signal selectively coupled to the signal processor as described below. The raw electrical measurement signal depicted in FIG. 6 represents an average of several individual signal acquisitions by the detector 4, 5. Raw electrical measurement signal 600 from the microphone's transducer associated with the PA pulse includes several groups of oscillations over time. A first oscillation group identified between arrows 630 is in the leading-edge-in-time of the raw electrical measurement signal 600 lasting about 10 μsec and is received between about 60 and 70 μsec. First oscillation group identified between arrows 630 corresponds to the acoustic signal 6 emitted by the thermal wave 230 and converted into an electrical signal by the transducer. A second oscillation group identified between arrows 640 lasts longer than 40 μsec and oscillates at lower frequency than the first oscillation group. Second oscillation group identified between arrows 640 is received after about 70 μsec and corresponds to transducer ringing in response to the acoustic signal emitted by the thermal wave.

Figure 7:
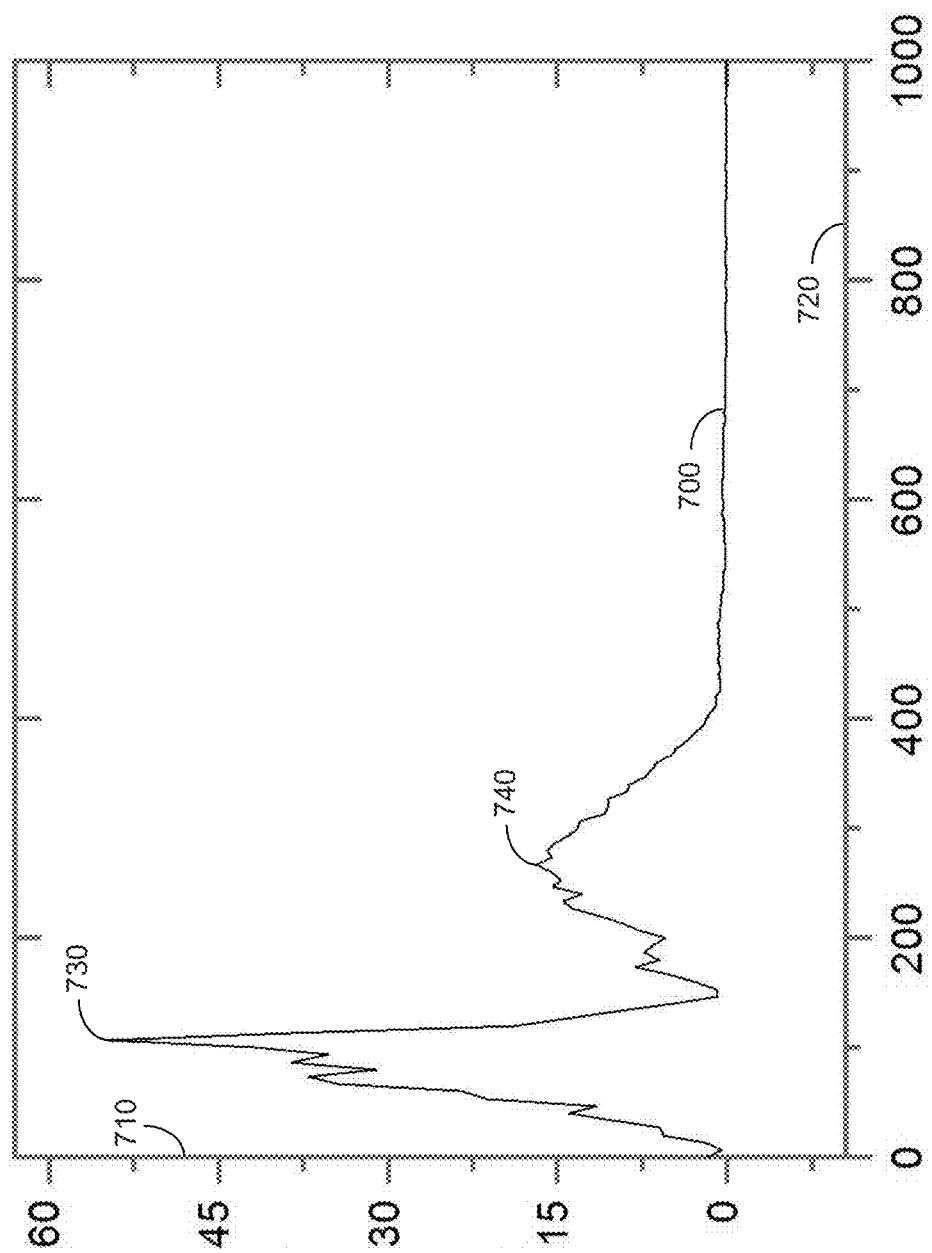
FIG. 7 depicts a raw electrical measurement signal in the frequency domain from the detector depicted in FIG. 4.

FIG. 7 depicts a raw electrical measurement signal in the frequency domain 700 from detector 4, 5 depicted in FIG. 4, acquired in a quiet laboratory environment. The vertical axis 710 of FIG. 7 represents raw electrical measurement signal amplitude in arbitrary units (a.u.) from about −10 to about 63 a.u., while the horizontal axis 720 represents frequency in kilo-Hertz (kHz) from 0 to 1000 kHz. The depicted signal is the Fourier transform of the raw electrical measurement signal from the detector depicted in FIG. 6. FIG. 7 depicts two amplitude peaks. The first amplitude peak 730 centered at about 110 kHz, which is higher in amplitude and narrower in frequency range than the second amplitude peak 740, may be caused by the transducer's resonance mode or transducer ringing corresponding to second oscillation group identified between arrows 640 in FIG. 6, and is not the signal most associated with characteristics of layer 2. In contrast, second amplitude peak 740 centered at about 280 kHz corresponds to first oscillation group identified between arrows 630 in FIG. 6 is more in response to the acoustic signal emitted by thermal wave 230 described above. Second amplitude peak 740 is thus most associated with characteristics of layer 2. FIG. 7 shows the first amplitude peak and the second amplitude peak are separated by about 150 kHz.

In one embodiment, the higher frequency response produced by the transducer and associated with the leading-edge-in-time of acoustic signal 6 is used by the PA system to measure the sample layer, while the lower frequency resonance mode of the transducer and much of the ambient acoustic noise from the industrial environment is selectively filtered out by the signal processor as described below. The higher frequency leading edge signal may be preferably used instead of the transducer's trailing edge resonance mode because the noise caused by the coil-coating process machinery is higher in amplitude at lower frequencies. Therefore, selecting the higher frequency leading edge signal in the higher frequency range where there is less noise is one contributor to improving the signal-to-noise ratio and thus the sensitivity of the PA system. In one embodiment, the frequency response of the transducer may be selected to be above about 150 kilohertz to be able to respond to the desired second amplitude peak measured in FIG. 7. Several commercially available air coupled microphones were evaluated for their ability to produce a desirable higher frequency response. A preferable microphone was determined to be an acoustic electret microphone model number FG23329 manufactured by Knowles Electronics, Inc.

Figure 8A:
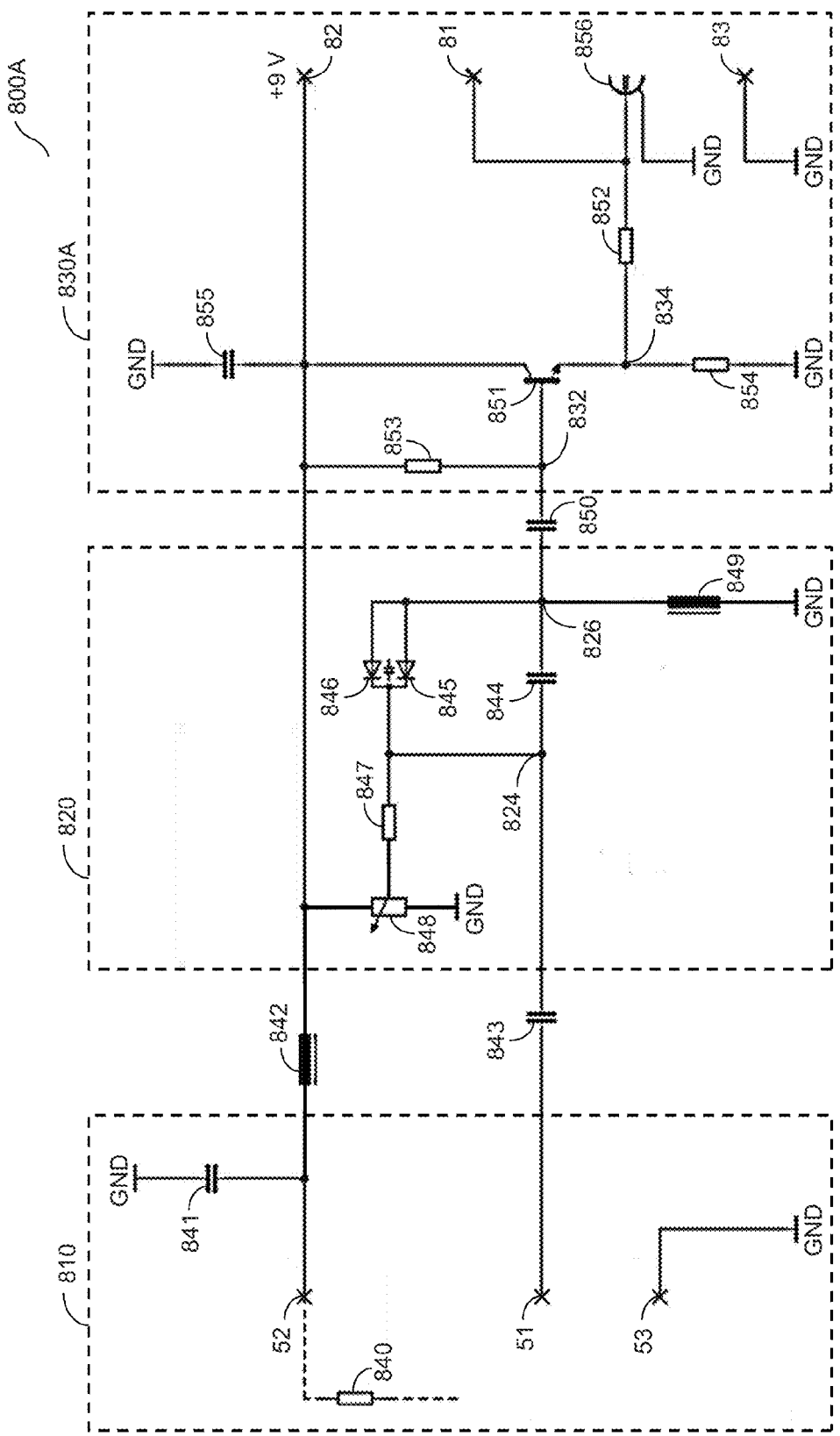
FIG. 8A depicts a schematic block diagram of a circuit portion of the signal processor depicted in FIG. 4, in accordance with one embodiment of the present invention.

FIG. 8A depicts a schematic block diagram of a circuit portion 800A of signal processor 7 depicted in FIG. 4, in accordance with one embodiment of the present invention. Circuit portion 800A of signal processor 7 includes a microphone high impedance input block 810 to signal processor 7, a filter block 820, and a 50 ohm converter and output of filtered signal block 830A. Microphone high impedance input block 810 includes three terminals 51-53, a microphone impedance resistor 840 used to represent the approximate microphone impedance, and a noise decoupling capacitor 841 between terminal 52 and ground. Terminals 51-53 are coupled to corresponding analog outputs of microphone 4. Terminal 53 couples the corresponding microphone terminal to ground. Terminal 52 couples the corresponding microphone terminal to a 9 V direct current (DC) supply at node 82 via alternating current (AC) blocking inductor 842. Terminal 51 couples the corresponding microphone terminal, i.e. the analog signal output of microphone 4, to a filter input 824 via AC signal coupling capacitor 843.

In one embodiment, filter block 820 may include a high-Q filter adapted to selectively pass a high frequency, leading-edge-in-time portion of the microphone's response signal produced by the transducer, while filtering out the lower frequency resonance of the transducer and industrial background noise to produce a filtered signal output. The high-Q filter may be coupled between filter input 824 and filter output 826. In one embodiment, high-Q filter includes a resonant inductance-capacitance (LC) filter having a quality factor greater than ten at 3 db below a peak amplitude of the higher frequency signal at a resonant frequency of the filter as measured with a sinusoidal signal generator (not shown) supplying the input signal by replacing microphone 4 at terminal 51 to facilitate filter response measurements. However, there may be impedance mismatches between the impedance of microphone 4 and the impedance looking into circuit portion 800A at terminal 51 that may cause degradation in the quality factor of the overall filter circuit when microphone 4 is attached to terminal 51 to supply the input signal instead of the sinusoidal signal used only for measurements. Circuit improvements are discussed below that improve the impedance matching at the filter inputs and outputs and lead to better signal characteristics.

High-Q filter may include a capacitance C coupled between filter input 824 and filter output 826. C is formed by the parallel combination of capacitor 844, and diodes 845, 846. Diodes 845, 846 may be operated as voltage controlled capacitors whose capacitance/voltage is determined by biasing circuit resistor 847 and variable potentiometer 848. Potentiometer 848 may be operated as a voltage divider coupled between ground and the 9 V supply such that potentiometer 848 provides a biasing voltage to the series combination of resistor 847 and the parallel combination of diodes 845, 846, which in turn are coupled to ground via an inductor 849. The value of C may thus be adjusted by potentiometer 848. Inductor 849 may be coupled between filter output 826 and ground. Inductor 849=L may resonate with capacitor C at a frequency of $f=(2\pi\sqrt{L*C})^{-1}$ to form the high-Q filter. For example, to resonate at a preferred 251 kHz with a Q-factor above 10, the values of LC in filter block 820 may be respectively chosen as 3.3 mH, and 112 pF.

In one embodiment, an input 832 of 50 ohm converter and output of filtered signal block 830A is coupled to filter output 826 via coupling capacitor 850, which in-turn drives the base of bipolar transistor 851 operated in source follower mode to isolate the impedance between input 832 and the emitter of transistor 851 at node 834. 50 ohm converter and output of filtered signal block 830A further includes impedance matching resistor 852 coupled between the emitter of transistor 851 and an output 81 of 50 ohm converter and output of filtered signal block 830A. The collector of transistor 851 may be coupled to the 9 V DV supply. 50 ohm converter and output of filtered signal block 830A further includes resistor 853 coupled between the base of transistor 851 and the 9V supply and resistor 854 coupled between the emitter and ground, which are chosen to bias transistor 851. A decoupling capacitor 855 is coupled between the 9 V supply at node 82 and ground to reduce noise. Thus, output 81 of 50 ohm converter and output of filtered signal block 830A provides a 50 ohm output via a BNC connector 856 to match a long cable run to the rest of signal processor 7, which may be located remotely from measurement head 9 and the moving metal coil 2, 13. The shield of BNC connector 856 may be coupled to ground 83.

In one embodiment, exemplary component values for circuit portion 800A depicted in FIG. 8A are tabulated in table 1 below.

TABLE 1

| | | |
|---|---|---|
| resistor | 840 | 10 kΩ |
| capacitor | 841 | 0.1 µF |
| inductor | 842 | 1 mH |
| capacitor | 843 | 47 nF |
| capacitor | 844 | 100 pF |
| resistor | 847 | 100 kΩ |
| potentiometer | 848 | 100 kΩ |
| inductor | 849 | 3.3 mH |
| capacitor | 850 | 0.1 µF |
| resistor | 852 | 50 Ω |
| resistor | 853 | 1 MegΩ |

TABLE 1-continued

| | | |
|---|---|---|
| resistor | 854 | 1 kΩ |
| capacitor | 855 | 0.1 µF |

Figure 8B:
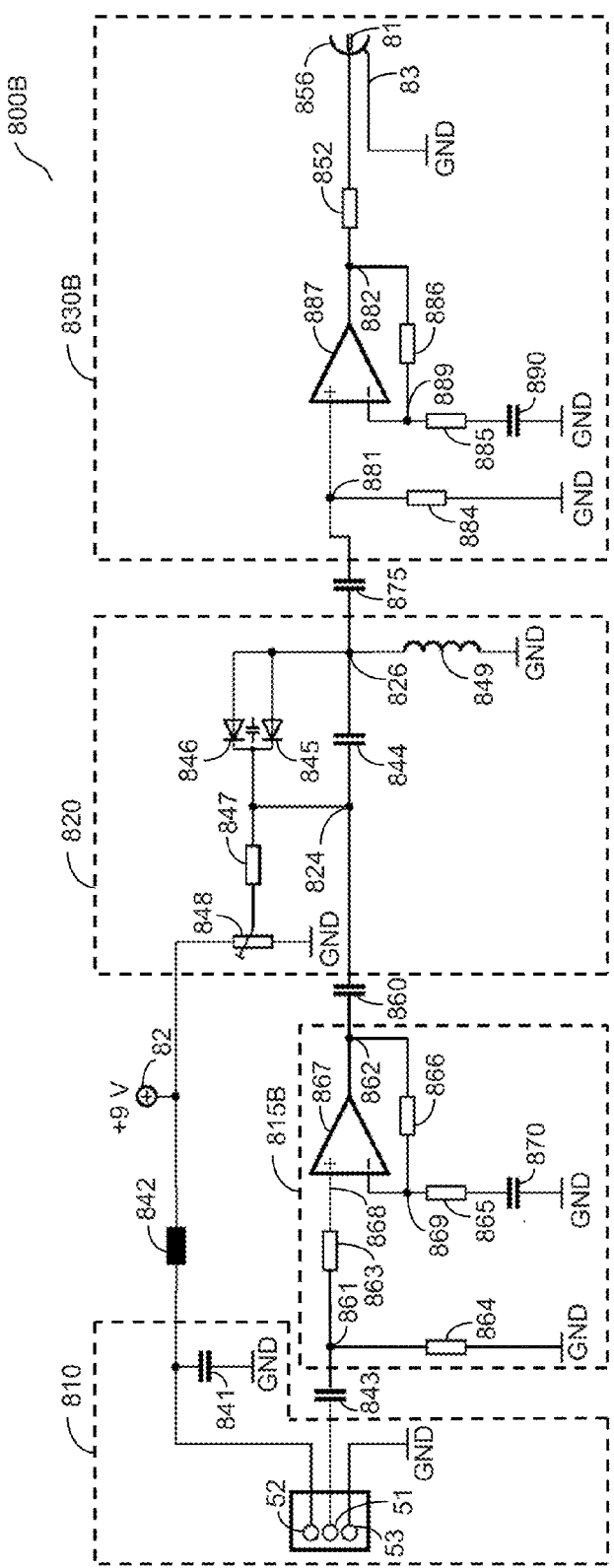
FIG. 8B depicts an improved schematic block diagram of a circuit portion of the signal processor depicted in FIG. 4, in accordance with one embodiment of the present invention.

FIG. 8B depicts an improved schematic block diagram of a circuit portion 800B of signal processor 7 depicted in FIG. 4, in accordance with one embodiment of the present invention. Circuit portion 800B has the same circuit elements and function as circuit portion 800A depicted in FIG. 8A with the exceptions described below to improve impedance matching at respective filter input and output 824, 826, which in-part lead to better signal performance. Circuit portion 800B includes an impedance converter 815B coupled between AC signal coupling capacitors 843, 860. AC signal coupling capacitor 860 is, in-turn, coupled to filter input 824.

Impedance converter 815B includes an input 861, an output 862, a multitude of resistors 863-866, an operational amplifier (op-amp) 867, and an AC signal coupling capacitor 870. The unfiltered signal from microphone 4 may be coupled through resistor 863 to non-inverting input 868 of op-amp 867. The impedance looking into the op-amp input is very high such that resistor 864, coupled between input 861 and ground, may be used to facilitate impedance matching between the impedance of the microphone and circuit portion 800B. An output of op-amp 867 may be coupled to output 862. Resistor 866 is coupled between the output of op-amp 867 and an inverting input 869 of op-amp 867 to provide negative feedback for op-amp 867. Resistor 865 is coupled in series with AC signal coupling capacitor 870 between inverting input 869 and ground. Resistors 865, 866 determine the amplifier signal gain. In one embodiment resistors 865, 866 may be chosen to configure the amplifier signal gain to be in the range between about 10 and 50 but preferably about 31. AC signal coupling capacitor 860 couples the amplified signal to filter input 824.

The output of the high-Q filter at 826 is coupled to an input 881 of a 50 ohm converter and output of filtered signal block 830B via an AC signal coupling capacitor 875. 50 ohm converter and output of filtered signal block 830B includes input 881, an output 882, a multitude of resistors 852, 884-886, an op-amp 887, an AC signal coupling capacitor 890, and BNC connector 856. The impedance looking into the op-amp input is very high such that resistor 884, coupled between input 881 and ground, may be used to facilitate impedance matching between the impedance of the high-Q filter and 50 ohm converter and output of filtered signal block 830B. Input 881 may be coupled directly to a non-inverting input of op-amp 887. An output of op-amp 887 may be coupled to output 882. Resistors 885, 886, AC signal coupling capacitor 890, and op-amp 887 may be configured and function in the same way as resistors 865, 866, AC signal coupling capacitor 870, and op-amp 867, except for amplifying the filtered signal. Output 882 is coupled to resistor 852 which provides impedance matching as described for circuit portion 800A in FIG. 8A.

In one embodiment, exemplary component values for circuit portion 800B depicted in FIG. 8B are tabulated in table 2 below.

TABLE 2

| | | |
|---|---|---|
| capacitor | 841 | 0.1 µF |
| inductor | 842 | 1 mH |
| capacitor | 843 | 47 nF |
| capacitor | 844 | 100 pF |
| resistor | 847 | 100 kΩ |

TABLE 2-continued

| | | |
|---|---|---|
| potentiometer | 848 | 100 kΩ |
| inductor | 849 | 3.3 mH |
| resistor | 852 | 50 Ω |
| capacitor | 860 | 47 nF |
| resistor | 863 | 1 kΩ |
| resistor | 864 | 100 kΩ |
| resistor | 865 | 33 Ω |
| resistor | 866 | 1 kΩ |
| capacitor | 870 | 0.1 µF |
| capacitor | 875 | 47 nF |
| resistor | 884 | 1 MegΩ |
| resistor | 885 | 33 Ω |
| resistor | 886 | 1 kΩ |
| capacitor | 890 | 0.1 µF |

In one embodiment, signal processor 7 may include µcontroller chip capable of executing program code stored in non-transient memory resident in the µcontroller chip or on a separate memory chip such as a flash memory. The program code may include the executable PA system commands and algorithms described below. Alternatively, and/or in combination with the processor, dedicated control logic such as available in a field programmable gate array (FPGA), or other hardwired control logic, may be used to execute the desired system commands and algorithms.

In one embodiment, signal processor 7 may be adapted to compensate the higher frequency resonance signal according to the energy of the pulse detected by energy detector 14 in the optics subsection to form a compensated signal that is substantially independent of a pulse-to-pulse fluctuation of the energy generated by the optics subsection. The laser pulse 12 has a certain pulse-to-pulse energy fluctuation. In non-destructive operation, the signal S associated with the filtered signal from microphone, will double with double the amount of energy E. For improved stability, the signal intensity is divided by the energy such that $S^* = S/E$, where $S^*$ is the energy normalized signal. This energy normalization means, the resulting normalized signal is fairly independent of pulse excitation energy. This normalization operation further provides the normalization of measurements to reference samples by multiplying the signal by an appropriate calibration factor as described below for system calibration.

Figure 9:
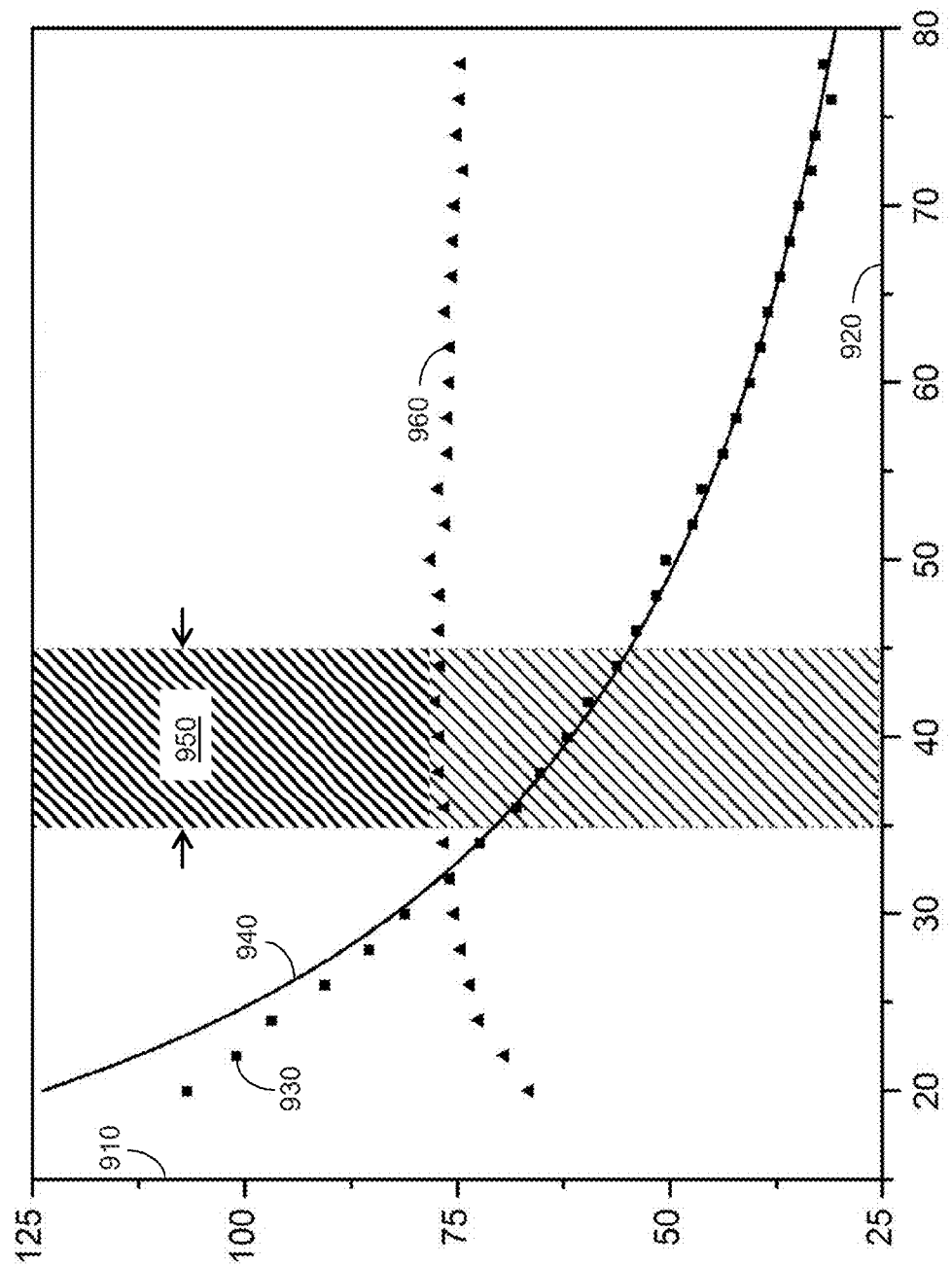
FIG. 9 depicts the dependence of the acoustic pressure amplitude on the detector to sample layer distance, in accordance with one embodiment of the present invention.

FIG. 9 depicts the dependence of the acoustic pressure amplitude on the detector to sample layer distance, in accordance with one embodiment of the present invention. The acoustic pressure amplitude in a.u. is depicted on the vertical axis 910 from 25 to 125 a.u., while the horizontal axis 920 depicts the detector to sample layer distance in millimeters (mm) from 15 to 80 mm. The detector to sample layer distance is very large compared to the sample layer thickness. In the coil coating process, the fast moving aluminum strip with sample layer frequently undergo mechanical shock and vibration that may cause fluctuations in the distance between the detector and the sample layer. Those distance fluctuations in-turn produce variations in the maximum pressure of the acoustic signal received by the detector, e.g. the raw acoustic pressure amplitude signal, that diminishes with increasing distance and is plotted as small squares 930 that indicate about 108 arbitrary units of pressure at a detector to sample layer distance of 20 mm, which diminishes to about 30 arbitrary units of pressure at a detector to sample distance of 80 mm. The acoustic pressure amplitude, y, versus detector to sample layer distance, x, may be established by previous calibration and is found to follow a hyperbolic curve fit above about 25 mm as indicated by the solid line 940 and approximated by a linear model over the range of the approximate normal working distance 950, as provided by the following equation $y=A_1+(P_1/x)$, where $P_1$ and $A_1$ are constants with values 2488.20049 and −0.57308, respectively. Approximate normal working distance 950 is depicted by the cross-hatched region between the horizontal arrows in a range between about 35 to 45 mm, although other working distance ranges may be used.

In one embodiment, the signal processor may calculate a distance between the detector and a region of the gas medium generating the thermal wave in accordance with a speed of the acoustic signal in the gas medium multiplied by a time of flight of the acoustic signal. The time and duration (less than about 0.1 μsec as described above) that the laser fires is controlled by signal processor 7 and are therefore known times. The time it takes the laser pulse signal traveling at the speed of light in the gas medium to reach the sample layer is negligibly small. The time it takes the irradiated layer to generate the thermal wave that generates the acoustic signal is also negligibly small. Therefore, the time the detector first receives the acoustic signal minus the time the laser fires is about equal to the time of flight of the acoustic signal, which may be calculated by the signal processor and may typically be about 120 μsec, which verifies the earlier assumptions about what is negligible. Because the speed of sound in gas medium 50, air, is known, signal processor 7 may then calculate the real time detector to sample layer distance by multiplying that speed of sound times the time of flight of the acoustic signal, resulting in a typical working distance value of about 41 mm for the above 120 μsec time of flight. The PA system is thus easily capable of taking a measurement once every millisecond, which readily provides a real-time analysis tool even for a fast moving layer 2 in the coil coating process.

In one embodiment, the signal processor may calculate the detector to sample layer distance, i.e. calculate a distance between the detector and a region of the gas medium generating the thermal wave, at periodic intervals or for each pulse. Then, the signal processor may compensate the maximum pressure or amplitude of each acoustic signal received in accordance with the distance and the predetermined hyperbolic model described above, which may be stored in the signal processor, to produce a resulting calculated compensated signal that is substantially independent of distance fluctuations above a distance of about 25 mm as indicated by the depicted triangles 960. In one embodiment the normal working distance is chosen between about 35 and 45 mm, which may be close to the lower end of the linear compensation range in order to have the advantage of a higher amplitude signal for better PA system sensitivity, while maintaining high compensation linearity in accordance with the better fit portion of the linear model described above. Although the sample distance may vary as much as +/−1 mm during the coil-coating process, a layer thickness measurement sensitivity of +/−2 nm may be achieved by the PA system.

Figure 10:
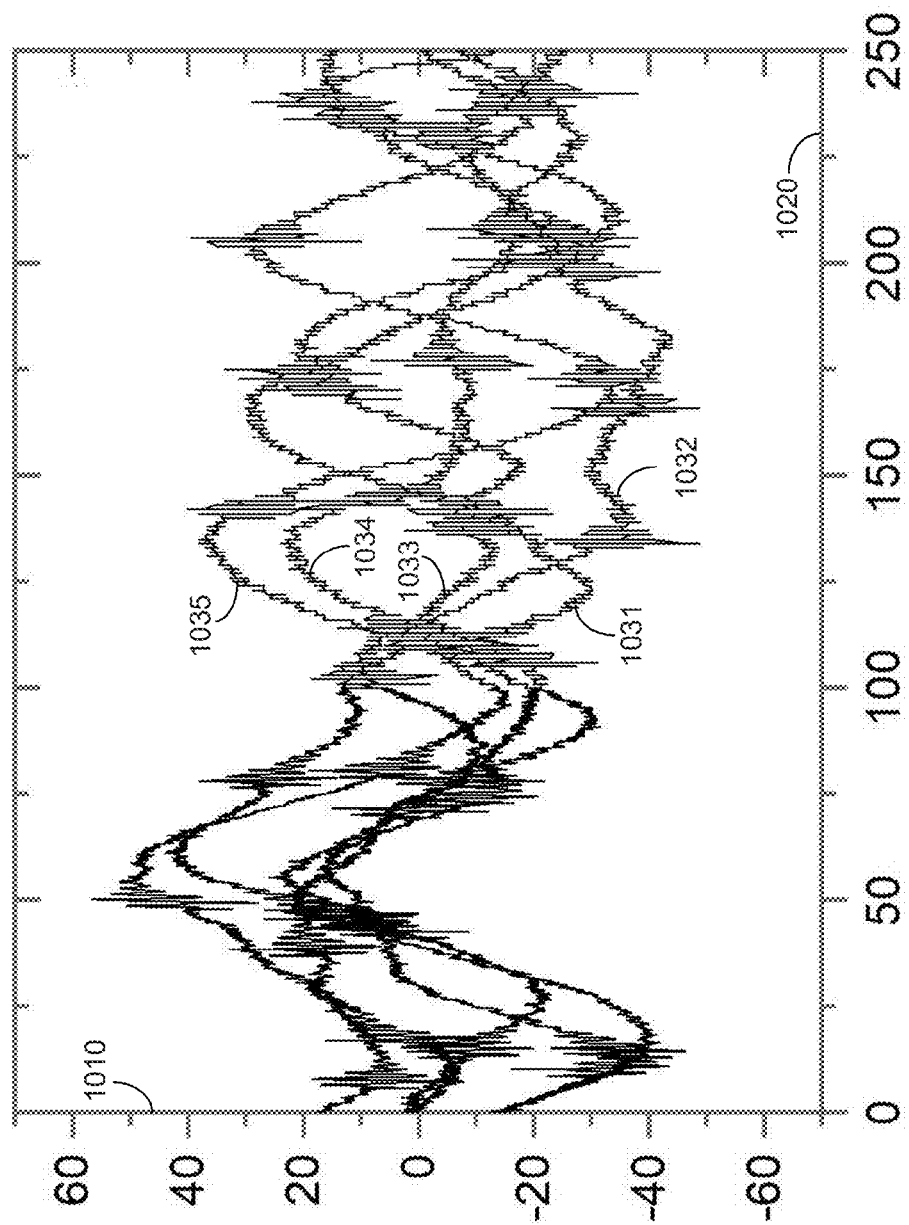
FIG. 10 depicts unfiltered ambient acoustic noise in an industrial application measured by the detector depicted in FIG. 4.

FIG. 10 depicts unfiltered ambient acoustic noise in an industrial application measured by the detector depicted in FIG. 4. The unfiltered ambient acoustic noise amplitude in mV is depicted on the vertical axis 1010 from −70 to 70 mV, while the horizontal axis 1020 depicts the elapsed time in is from 0 to 250 μs. The coil coating process machinery produces a background noise that is strong in the ultrasonic frequency range. Five measurements of the unfiltered ambient acoustic noise amplitude, 1031, 1032, 1033, 1034, 1035, were taken at different times during the coil coating process are shown, which indicate many noise pulses having a period greater than about 2 μsec or frequency below about 500 kHz, which overlaps the ultrasonic frequency range, which the PA system uses as will be shown below. In one embodiment, the signal processor was adapted to improve a signal to noise ratio of the signal detected, which acoustic signal received by the detector to form a filtered signal as described below, which in-turn, removed most of the unwanted noise frequencies generated by the coil-coating process.

Figure 11A:
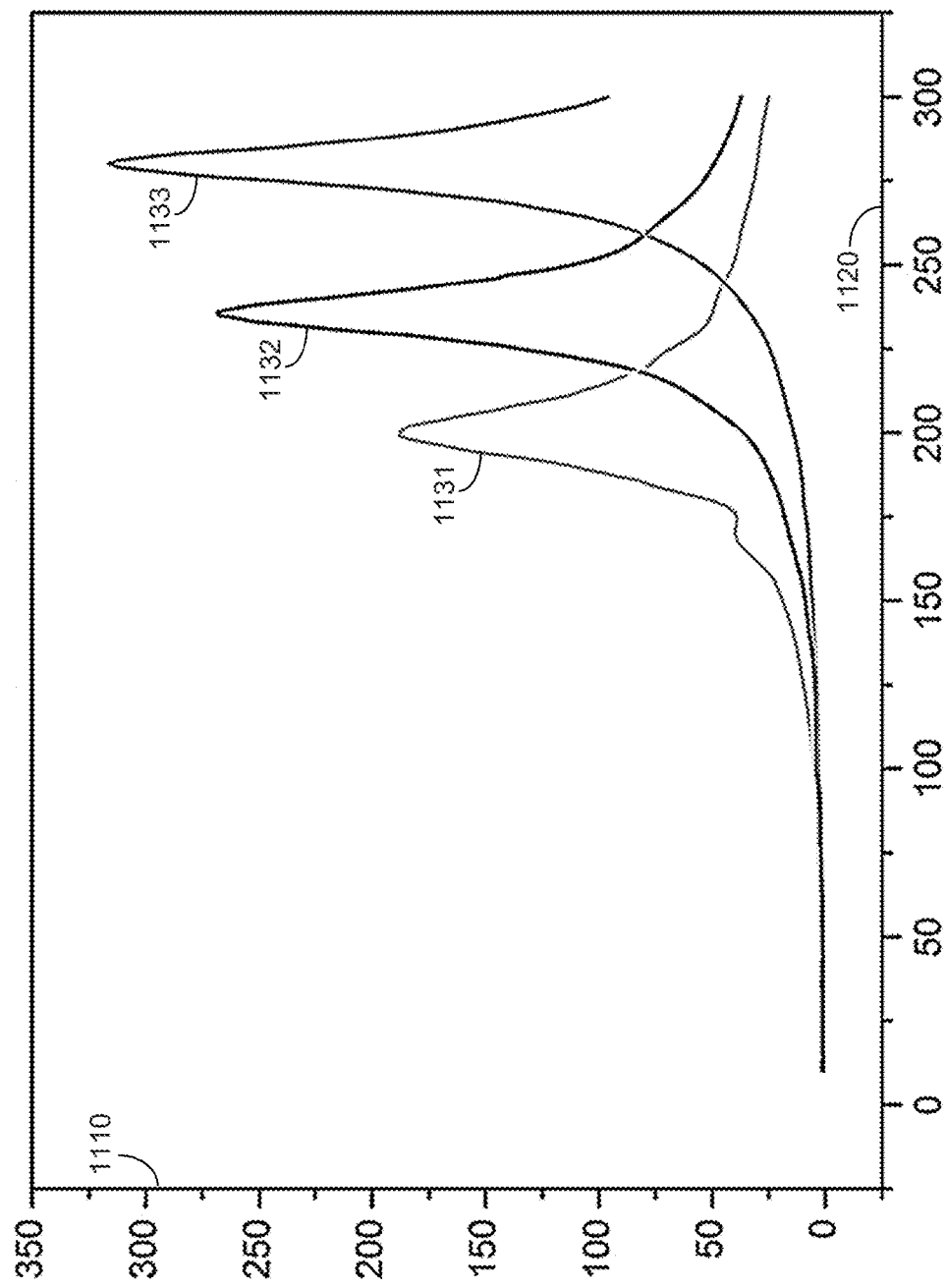
FIG. 11A depicts a response of a high-quality-factor (high-Q) filter depicted in FIG. 8A, in accordance with one embodiment of the present invention.

FIG. 11A depicts a response of high-Q filter 820 depicted in FIGS. 8A-8B, in accordance with one embodiment of the present invention. Signal processor 7 may include the high-Q filter adapted to selectively pass the higher frequency, leading-edge-in-time signal from the transducer. Because typical off-the-shelf bandpass filters were not found to have a high enough Q-factor, that is, enough discrimination to pass a narrow passband in the desired frequency range of the high frequency transducer signal output, while severely filtering out other undesired noise frequencies and the resonance signal from transducer 56, the simple proprietary resonant LC circuit described in reference to FIGS. 8A-8B is used. Without microphone 4, the response to a sinusoidal 50 mV signal input of the resonant LC high-Q filter 820 is depicted in FIG. 11A where the filter response signal in mV is depicted on the vertical axis 1110 from −25 to 350 mV, and the excitation frequency in kHz is depicted on the horizontal axis 1120 from 0 to 325 kHz, for three different filter settings tuned respectively at 200, 235, 280 kHz using potentiometer R2 and depicted by filter response signals 1131, 1132, 1133 respectively.

Applying the definition that Q-factor is defined by the center of the passband divided by the passband at −3 dB and that −3 dB is defined where the peak amplitude is reduced by a factor of 1/1.413 yields the resultant Q-factors of about 10 and 28 respectively for the 200 kHz and 280 kHz resonant frequencies of the proprietary resonant LC filter response. Thus, in one embodiment, the filter includes a resonant LC filter having a quality factor greater than ten at 3 db below a peak amplitude of the high frequency transducer response at a resonant frequency of the filter, which may be set preferably at 251 kHz to pass the high frequency transducer response depicted in FIG. 7 of the selected microphone.

Figure 11B:
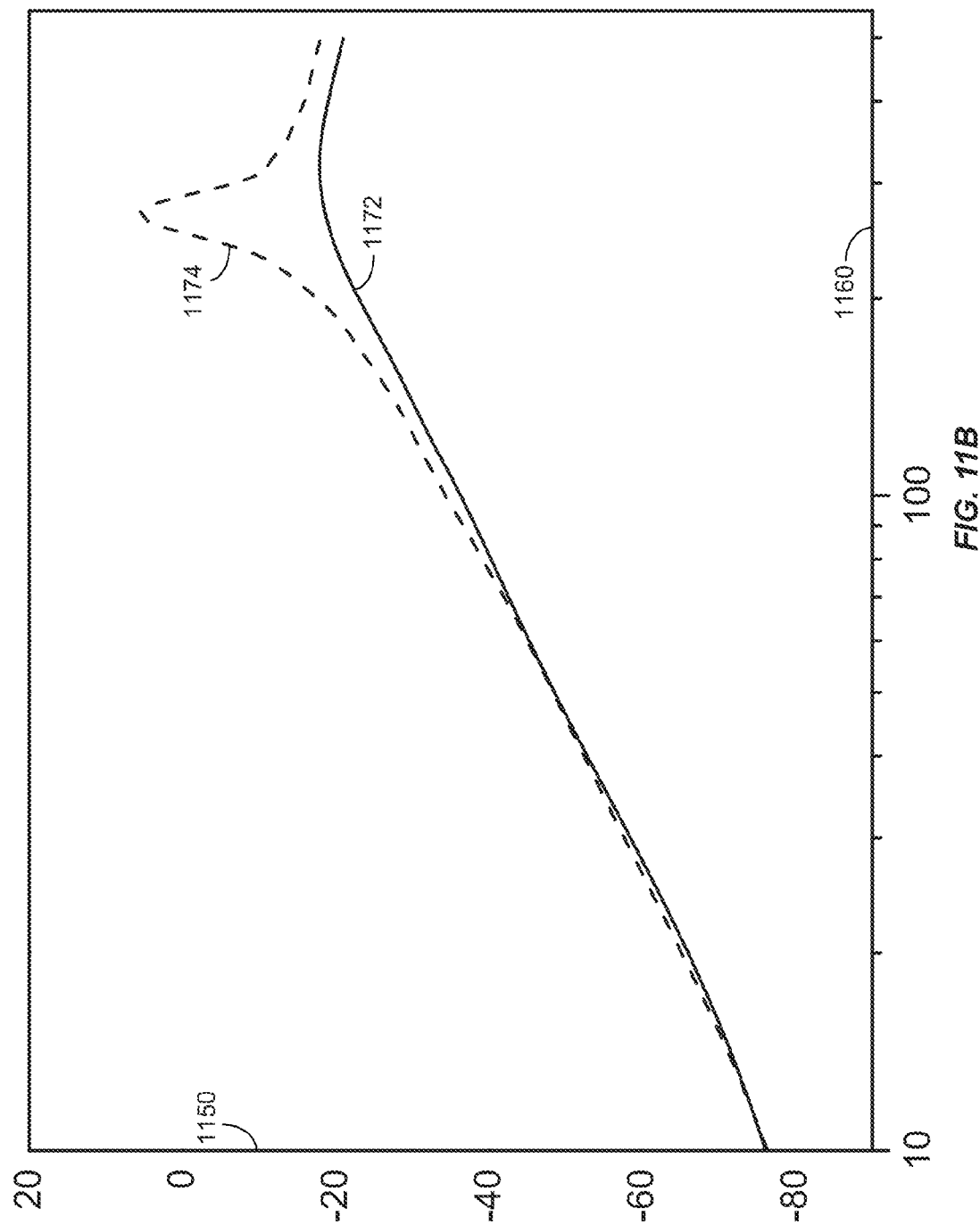
FIG. 11B depicts a comparison of the simulated behavior over frequency of the circuit portions depicted in FIGS. 8A-8B, in accordance with one embodiment of the present invention.

FIG. 11B depicts a comparison of the simulated behavior over frequency of the circuit portions 800A, 800B depicted in FIGS. 8A-8B respectively, in accordance with one embodiment of the present invention. As described above, the ability of the high-Q filter 820 depicted in FIGS. 8A-8B to provide a steep roll-off characteristic around the resonant frequency, or a high discrimination, is responsive to the surrounding circuitry including the impedance matching at input 824 of high-Q filter 820. In FIG. 11B, the simulated signal response in decibels (dB) of the overall circuit portions 800A, 800B from a simulated signal input via microphone 4 is depicted on the vertical axis 1150 from about −90 to 20 dB, while the horizontal axis 1160 depicts the simulated frequency in kHz from about 10 to 550 kHz.

The simulated frequency response of the circuit portion 800A is depicted by the solid line 1172 and depicts a peak signal at about −20 dB at 250 kHz, which falls off below 250 kHz at a rate of about 0.15 db/kHz. The simulated frequency response of the improved circuit portion 800B is depicted by the dashed line 1174 and depicts a higher peak signal at about 5 dB at 250 kHz, which falls off for about 50 kHz below 250 kHz at a higher rate of about 0.8 db/kHz until meeting up with and matching the frequency response of the circuit portion 800A below about 100 kHz. The improved circuit portion 800B is thus expected to provide more desirable filtering characteristics than circuit portion 800A, based on these circuit simulation results.

Figure 12:
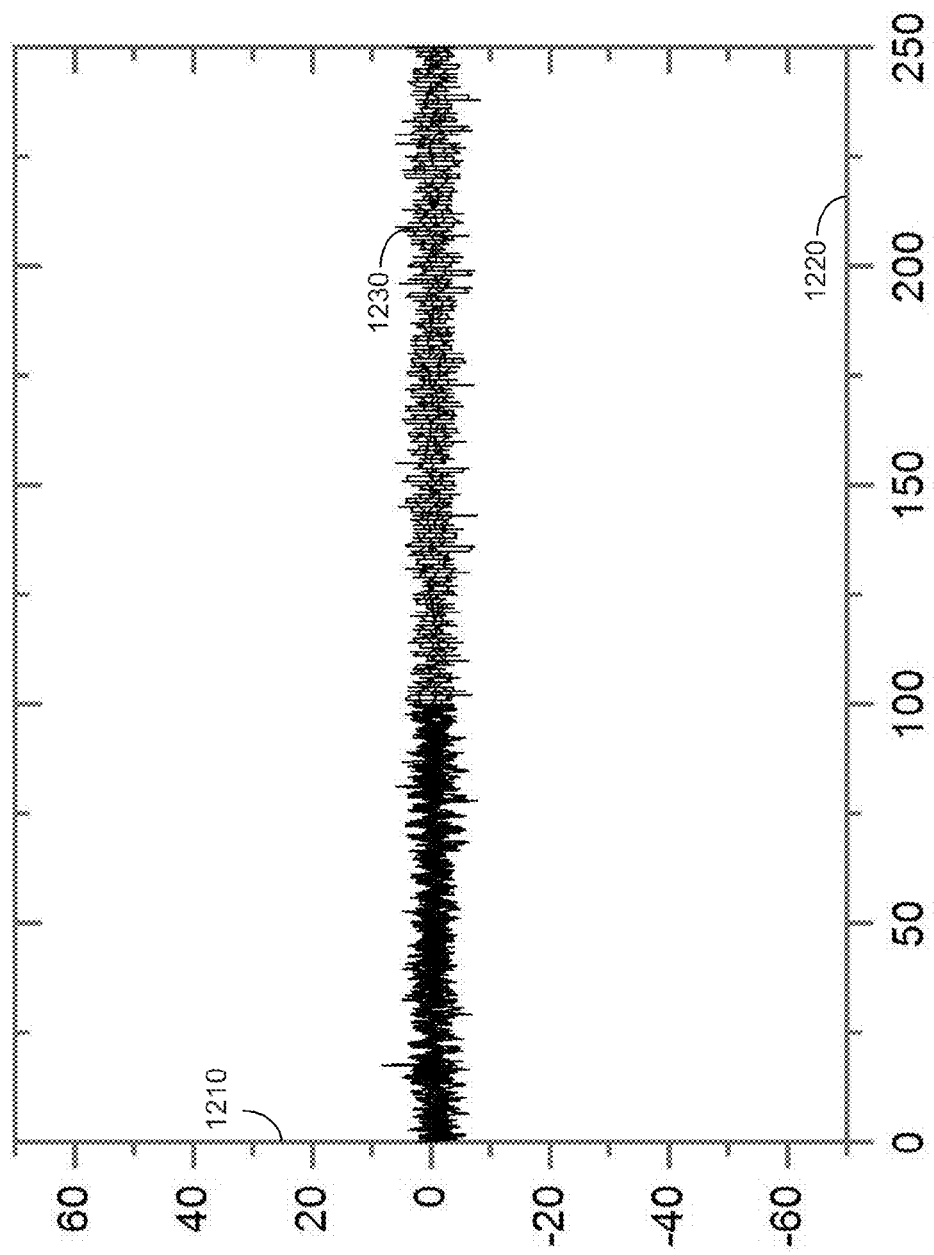
FIG. 12 depicts the effectiveness of the high-Q filter in removing the ambient acoustic noise in the industrial application depicted in FIG. 10, in accordance with one embodiment of the present invention.

FIG. 12 depicts the effectiveness of the high-Q filter corresponding to the response depicted in FIG. 11A in removing the ambient acoustic noise in the industrial application depicted in FIG. 10, in accordance with one embodiment of the present invention. The vertical axis 1210 of FIG. 12 represents the noise signal amplitude in mV from −70 to 70 mV, while the horizontal axis 1220 represents elapsed time in μs from 0 to 250 μs. The result of five different measurements 1230 using the proprietary resonant LC filter in the same acoustic noise environment depicted in FIG. 10 is reduced from a peak amplitude of about 50 mV to about 5 mV in the desired passband at 251 kHz.

Figure 13:
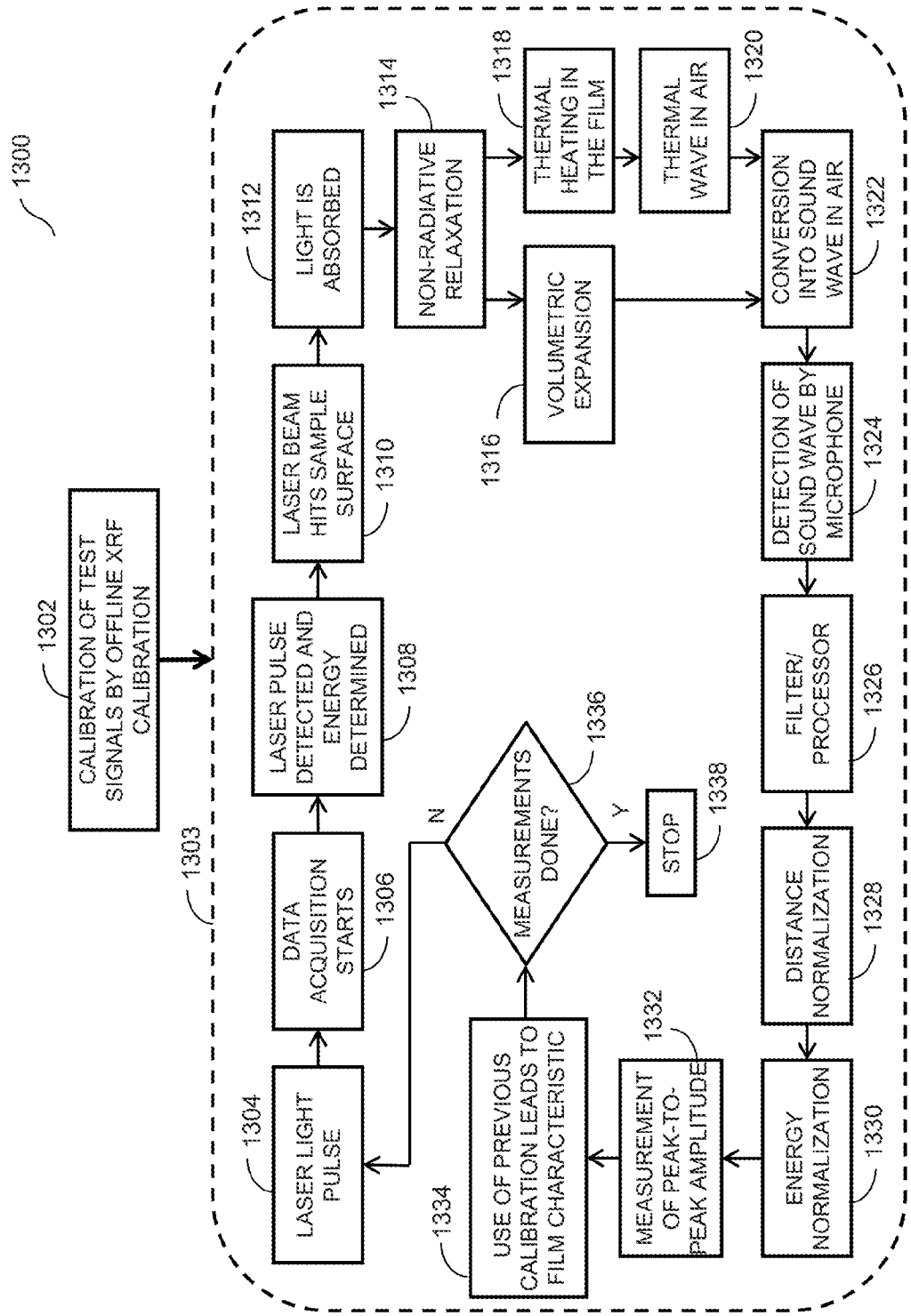
FIG. 13 depicts a measurement method using the photo-acoustic measuring apparatus depicted in FIG. 4, in accordance with one embodiment of the present invention.

FIG. 13 depicts a measurement method 1300 using the photo-acoustic measuring apparatus depicted in FIG. 4, in accordance with one embodiment of the present invention. Referring simultaneously to FIGS. 4 and 13, measurement method 1300 includes a calibration 1302 preceding a measurement loop 1303. Calibration 1302 may calibrate test signals of the PA system by using XRF to determine an accurate layer 2 thickness off-line, that is, in a laboratory setting and not during the noisy coil coating process. The measured signal versus actual characteristic value such as thickness may be stored as a look-up table or as a calculated calibration model in the memory of signal processor 7. Measurement loop 1303 includes the following steps that may be performed while the PA system is on-line during the coil coating process.

The laser light is pulsed 1304 at predetermined periods such as once every millisecond. Then data acquisition starts 1306. The laser pulse may be detected and the pulse energy determined 1308 by energy detector 14. Laser beam pulse 12 then hits 1310 the sample surface of layer 2 and the laser light is absorbed 1312 by layer 2. Non-radiative relaxation 1314 occurs. Then simultaneously there is volumetric expansion 1316, which causes a small acoustic signal, and thermal heating 1318 in the film, which causes a thermal wave 1320 in the air. Thermal wave 1320 in the air is converted 1322 into most of acoustic signal 6, i.e. a sound wave.

The sound wave or acoustic signal 6 is transmitted during a time of flight through the air to detector 4,5 and detected 1324 by microphone 4. The detected electrical signal from the transducer in the microphone such as depicted in FIGS. 6-7 is filtered 1326 by high-Q filter 820 in signal processor 7, which then performs distance normalization 1328 and energy normalization 1330 in any order. Then the peak to peak amplitude of the normalized signal is measured 1332. Signal processor 7 then uses 1334 the previously determined calibration look up table or calibration model to determine the film characteristic of layer 2. If the PA system determines 1336 the measurements are not done, then the measurement loop continues by starting over at pulsing 1304 the next laser light pulse 12. The method stops 1338 when the measurements are done.

Figure 14:
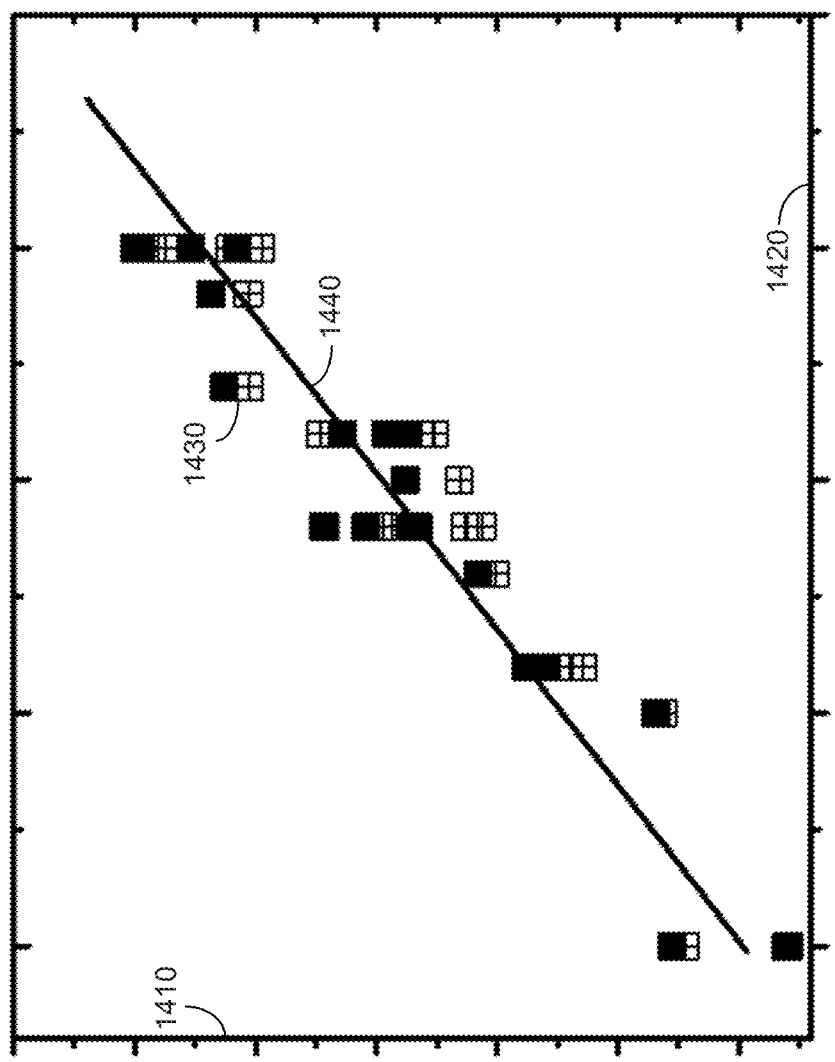
FIG. 14 depicts a comparison between measurements obtained using the photo-acoustic measuring apparatus depicted in FIG. 4 to measurements using an XRF technique, in accordance with one embodiment of the present invention.

FIG. 14 depicts a comparison between measurements obtained using the photo-acoustic measuring apparatus depicted in FIG. 4 to measurements using an XRF technique. The maximum pressure amplitude in arbitrary units is represented on the vertical axis 1410 and the measured off-line XRF film characteristic for the chemical composition of zirconium contained in the film in milligram per meter squared (mg/m$^2$) is represented on the horizontal axis 1420. The plotted data points from several samples 1430 show a linear correlation characteristic 1440 that may be used as a model to calibrate the normalized acoustic signal of PA system 1.

FIG. 15 depicts a measuring device 1502 including a multitude of different detectors 1504, 1506, 1508. A measuring device 1502 may include a multitude of different detectors 1504, 1506, 1508 each associated with a different one of a multitude of pulses.

The above embodiments of the present invention are illustrative and not limiting. Various alternatives and equivalents are possible. Although, the invention has been described with reference to a certain arrangement of optical components by way of an example, it is understood that the invention is not limited by the optical component arrangement as long as a non-destructive electromagnetic pulse with desired characteristics is provided. Although, the invention has been described with reference to a dry solid sample layer by way of an example, it is understood that the invention is not limited by the form of the layer, which may be a solid, a gel, a liquid, and/or a powder. The embodiments described herein have been directed to measuring a conversion coating applied in a coil-coating process onto an aluminum strip but are not limited thereto. The embodiments of the present invention are not limited by the type of substrate supporting the sample layer. The embodiments described herein may be used whenever a non-contact, non-destructive measurement of sub 100 nm layers, which may be moving and/or have a rough surface are found useful. For example, the embodiments described herein may be found useful in measuring drying or polymerization processes, measuring chemical kinetics, defining optical and/or thermal properties of layers, the analysis of composite-systems and the characterization of products from atomic layer deposition processes. Other additions, subtractions, or modifications are obvious in view of the present disclosure and are intended to fall within the scope of the appended claims. The scope of the invention should, therefore, be determined not with reference to the above description, but instead should be determined with reference to the pending claims along with their full scope or equivalents.

What is claimed is:

1. A measuring device for non-mechanical-contact measurement of a layer, the measuring device comprising:
    a light source operative to generate a pulse adapted to interact with the layer so as to generate a thermal wave in a gas medium present adjacent the layer, said thermal wave causing an acoustic signal to be generated; and
    a detector adapted to detect a first signal responsive to the acoustic signal, said detector not being in mechanical contact with the layer, wherein said first signal is representative of the measured layer;
    wherein the pulse is associated with an absorption of the pulse within the layer, the absorption being substantially greater than an absorption of the pulse within a substrate in mechanical contact with the layer, wherein the layer is disposed between the substrate and the gas medium.

2. The measuring device of claim 1, wherein the pulse is adapted to interact with the layer without permanently altering the layer.

3. The measuring device of claim 1, wherein a wavelength of the pulse is associated with a penetration depth of the pulse in the layer, the penetration depth being greater than a thickness of the layer.

4. The measuring device of claim 1, wherein a temporal width of the pulse is associated with a thermal diffusion length of the layer, the thermal diffusion length being substantially equal to a thickness of the layer.

5. The measuring device of claim 1, wherein the detector comprises:
   a transducer adapted to have a frequency response greater than a frequency range of a noise ambient in the vicinity of the detector and to generate the first signal.

6. The measuring device of claim 1, wherein the detector comprises:
   a sound coupler adapted to direct a portion of the acoustic signal to the detector.

7. The measuring device of claim 1, wherein the light source is further operative to generate a plurality of pulses each having different associated characteristics selected to interact with a plurality of different associated constituents of the layer, said measuring device including a plurality of different detectors each associated with a different one of the plurality of pulses.

8. The measuring device of claim 1 further comprising a signal processor adapted to:
   improve a signal to noise ratio of the first signal to form a second signal;
   calculate a distance between the detector and a region of the gas medium generating the thermal wave;
   compensate the second signal in accordance with the distance to produce a third signal that is substantially independent of a fluctuation of the distance; and
   determine a measurement responsive to a composition and thickness of the film in accordance with an amplitude of the third signal and a predetermined look-up table.

9. The measuring device of claim 8, wherein the signal processor is further adapted to calculate the distance in accordance with a speed of the acoustic signal in the gas medium multiplied by a time of flight of the acoustic signal.

10. A method for non-mechanical-contact measurement of a layer, the method comprising:
    generating a pulse adapted to interact with the layer to generate a thermal wave in a gas medium present adjacent the layer, thereby causing an acoustic signal to be generated; and
    detecting a first signal responsive to the acoustic signal without mechanically contacting the layer, wherein said first signal is representative of the measured layer;
    wherein the pulse is associated with an absorption of the pulse within the layer, the absorption being substantially greater than an absorption of the pulse within a substrate in mechanical contact with the layer, wherein the layer is disposed between the substrate and the gas medium.

11. The method of claim 10, wherein the pulse interacts with the layer without permanently altering the layer.

12. The measuring device of claim 10, wherein a wavelength of the pulse is associated with a penetration depth of the pulse in the layer, the penetration depth being greater than a thickness of the layer.

13. The measuring device of claim 10, wherein a temporal width of the pulse is associated with a thermal diffusion length of the layer, the thermal diffusion length being substantially equal to a thickness of the layer.

14. The method of claim 10 further comprising:
    generating the first signal using a transducer having a frequency response greater than a frequency range of a noise ambient in the vicinity of the detector.

15. The method of claim 10 further comprising:
    directing a portion of the acoustic signal to a detector.

16. The method of claim 10 further comprising:
    generating a plurality of pulses each having different associated characteristics selected to interact with a plurality of different associated constituents of the layer; and
    using a plurality of different detectors each associated with a different one of the plurality of pulses.

17. The method of claim 10 further comprising:
    improving a signal to noise ratio of the first signal to form a second signal;
    calculating a distance between a detector and a region of the gas medium generating the thermal wave;
    compensating the second signal in accordance with the distance to produce a third signal that is substantially independent of a fluctuation of the distance; and
    determining a measurement responsive to a composition and thickness of the film in accordance with an amplitude of the third signal and a predetermined look-up table.

18. The method of claim 17 further comprising:
    calculating the distance in accordance with a speed of the acoustic signal in the gas medium multiplied by a time of flight of the acoustic signal.

* * * * *

UNITED STATES PATENT AND TRADEMARK OFFICE
CERTIFICATE OF CORRECTION

PATENT NO. : 9,791,419 B2  
APPLICATION NO. : 14/623181  
DATED : October 17, 2017  
INVENTOR(S) : Heinrich Prinzhorn et al.

Page 1 of 1

It is certified that error appears in the above-identified patent and that said Letters Patent is hereby corrected as shown below:

In the Claims

In Column 22, Line 7 of Claim 12, please delete "The measuring device of" and replace with -- The method of --

In Column 22, Line 11 of Claim 13, please delete "The measuring device of" and replace with -- The method of --

Signed and Sealed this  
Seventh Day of May, 2019

Andrei Iancu  
*Director of the United States Patent and Trademark Office*